(12) United States Patent
Atalar et al.

(10) Patent No.: US 8,433,421 B2
(45) Date of Patent: *Apr. 30, 2013

(54) MRI-SAFE HIGH IMPEDANCE LEAD SYSTEMS

(75) Inventors: Ergin Atalar, Ankara (TR); Justin Allen, Baltimore, MD (US); Paul Bottomley, Columbia, MD (US); William Eldelstein, Baltimore, MD (US); Parag V. Karmarkar, Columbia, MD (US)

(73) Assignees: Boston Scientific Neuromodulation Corporation, Valencia, CA (US); MRI Interventions, Inc., Memphis, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/290,822

(22) Filed: Nov. 7, 2011

(65) Prior Publication Data

US 2012/0071953 A1 Mar. 22, 2012

Related U.S. Application Data

(63) Continuation of application No. 12/090,583, filed as application No. PCT/US2006/041109 on Oct. 20, 2006, now Pat. No. 8,055,351.

(60) Provisional application No. 60/729,020, filed on Oct. 21, 2005.

(51) Int. Cl.
*A61N 1/00* (2006.01)

(52) U.S. Cl.
USPC .......................................................... 607/63

(58) Field of Classification Search ..................... 607/63
See application file for complete search history.

(56) References Cited

U.S. PATENT DOCUMENTS

| 5,697,958 | A | 12/1997 | Paul et al. |
| 6,050,992 | A | 4/2000 | Nichols |
| 6,167,311 | A | 12/2000 | Rezai |

(Continued)

FOREIGN PATENT DOCUMENTS

| WO | 03063946 | 8/2003 |
| WO | 2004095281 A2 | 11/2004 |

(Continued)

OTHER PUBLICATIONS

Bottomley, P. A., "Designing passive MRI-safe implantable conducting leads with electrodes," Med. Phys. 37(7), Jul. 2010, pp. 3828-3843.

(Continued)

*Primary Examiner* — George Manuel
(74) *Attorney, Agent, or Firm* — Frommer Lawrence & Haug LLP; Bruce E. Black

(57) ABSTRACT

Some embodiments are directed to MRI/RF compatible medical interventional devices. A plurality of spaced apart high impedance circuit segments are configured to have a high impedance at a high range of radiofrequencies and a low impedance at a low range of frequencies. The high impedance circuit segments may comprise co-wound coiled inductors and can reduce, block or inhibit RJ-transmission along the lead system (20) during exposure to RF associated with a high-Held magnet MRI systems, while permitting passage of low frequency physiologic signals, treatments and/or stimuli. The devices can include at least one electrode.

20 Claims, 24 Drawing Sheets

U.S. PATENT DOCUMENTS

| | | |
|---|---|---|
| 6,284,971 B1 | 9/2001 | Atalar et al. |
| 6,356,786 B1 | 3/2002 | Rezai et al. |
| 6,405,079 B1 | 6/2002 | Ansarinia |
| 6,438,423 B1 | 8/2002 | Rezai et al. |
| 6,526,318 B1 | 2/2003 | Ansarinia |
| 6,539,263 B1 | 3/2003 | Schiff et al. |
| 6,584,351 B1 | 6/2003 | Ekwal |
| 6,609,030 B1 | 8/2003 | Rezai et al. |
| 6,708,064 B2 | 3/2004 | Rezai |
| 6,725,092 B2 | 4/2004 | MacDonald et al. |
| 6,765,779 B2 | 7/2004 | Stevenson et al. |
| 6,765,780 B2 | 7/2004 | Brendel |
| 6,888,715 B2 | 5/2005 | Stevenson et al. |
| 6,925,328 B2 | 8/2005 | Foster et al. |
| 6,987,660 B2 | 1/2006 | Stevenson et al. |
| 7,012,192 B2 | 3/2006 | Stevenson et al. |
| 7,013,180 B2 | 3/2006 | Villaseca et al. |
| 7,035,076 B1 | 4/2006 | Stevenson |
| 7,035,077 B2 | 4/2006 | Brendel |
| 7,038,900 B2 | 5/2006 | Stevenson et al. |
| 7,136,273 B2 | 11/2006 | Stevenson et al. |
| 7,164,950 B2 * | 1/2007 | Kroll et al. ............... 607/36 |
| 7,199,995 B2 | 4/2007 | Stevenson |
| 7,310,216 B2 | 12/2007 | Stevenson et al. |
| 7,489,495 B2 | 2/2009 | Stevenson |
| 7,535,693 B2 | 5/2009 | Stevenson et al. |
| 7,623,335 B2 | 11/2009 | Stevenson et al. |
| 7,623,336 B2 | 11/2009 | Stevenson et al. |
| 7,689,288 B2 | 3/2010 | Stevenson et al. |
| 7,751,903 B2 | 7/2010 | Stevenson et al. |
| 7,765,005 B2 | 7/2010 | Stevenson |
| 7,787,958 B2 | 8/2010 | Stevenson |
| 7,822,460 B2 | 10/2010 | Halperin et al. |
| 7,844,319 B2 | 11/2010 | Susil et al. |
| 7,853,324 B2 | 12/2010 | Stevenson et al. |
| 7,853,325 B2 | 12/2010 | Dabney et al. |
| 7,899,551 B2 | 3/2011 | Westlund et al. |
| 7,916,013 B2 | 3/2011 | Stevenson |
| 7,917,219 B2 | 3/2011 | Stevenson et al. |
| 8,055,351 B2 | 11/2011 | Atalar et al. |
| 2002/0038135 A1 | 3/2002 | Connelly et al. |
| 2003/0036776 A1 | 2/2003 | Foster et al. |
| 2003/0144720 A1 | 7/2003 | Villaseca et al. |
| 2003/0144721 A1 | 7/2003 | Villaseca et al. |
| 2003/0179536 A1 | 9/2003 | Stevenson et al. |
| 2003/0213604 A1 | 11/2003 | Stevenson et al. |
| 2003/0213605 A1 | 11/2003 | Brendel et al. |
| 2004/0201947 A1 | 10/2004 | Stevenson et al. |
| 2004/0257747 A1 | 12/2004 | Stevenson et al. |
| 2005/0007718 A1 | 1/2005 | Stevenson et al. |
| 2005/0190527 A1 | 9/2005 | Stevenson et al. |
| 2005/0201039 A1 | 9/2005 | Stevenson et al. |
| 2005/0219787 A1 | 10/2005 | Stevenson et al. |
| 2005/0222642 A1 | 10/2005 | Przybyszewski et al. |
| 2005/0222647 A1 | 10/2005 | Wahlstrand et al. |
| 2005/0247475 A1 | 11/2005 | Stevenson et al. |
| 2005/0248907 A1 | 11/2005 | Stevenson et al. |
| 2006/0028784 A1 | 2/2006 | Brendel |
| 2006/0085043 A1 | 4/2006 | Stevenson |
| 2006/0212096 A1 | 9/2006 | Stevenson |
| 2006/0221543 A1 | 10/2006 | Stevenson et al. |
| 2006/0252314 A1 | 11/2006 | Atalar et al. |
| 2007/0019362 A1 | 1/2007 | Stevenson et al. |
| 2007/0035910 A1 | 2/2007 | Stevenson |
| 2007/0112398 A1 | 5/2007 | Stevenson et al. |
| 2007/0123949 A1 | 5/2007 | Dabney et al. |
| 2007/0279834 A1 | 12/2007 | Stevenson et al. |
| 2007/0288058 A1 | 12/2007 | Halperin et al. |
| 2008/0039709 A1 | 2/2008 | Karmarkar |
| 2008/0049376 A1 | 2/2008 | Stevenson et al. |
| 2008/0065181 A1 | 3/2008 | Stevenson |
| 2008/0071313 A1 | 3/2008 | Stevenson et al. |
| 2008/0116997 A1 | 5/2008 | Dabney et al. |
| 2008/0119919 A1 | 5/2008 | Atalar et al. |
| 2008/0132987 A1 | 6/2008 | Westlund et al. |
| 2008/0161886 A1 | 7/2008 | Stevenson et al. |
| 2008/0195180 A1 | 8/2008 | Stevenson et al. |
| 2008/0269591 A1 | 10/2008 | Halperin et al. |
| 2009/0116167 A1 | 5/2009 | Stevenson et al. |
| 2009/0259265 A1 | 10/2009 | Stevenson et al. |
| 2010/0016936 A1 | 1/2010 | Stevenson et al. |
| 2010/0023000 A1 | 1/2010 | Stevenson et al. |
| 2010/0023095 A1 | 1/2010 | Stevenson et al. |
| 2010/0060431 A1 | 3/2010 | Stevenson et al. |
| 2010/0160997 A1 | 6/2010 | Johnson et al. |
| 2010/0168821 A1 | 7/2010 | Johnson et al. |
| 2010/0174349 A1 | 7/2010 | Stevenson et al. |
| 2010/0191236 A1 | 7/2010 | Johnson et al. |
| 2010/0191306 A1 | 7/2010 | Stevenson et al. |
| 2010/0194541 A1 | 8/2010 | Stevenson et al. |
| 2010/0198312 A1 | 8/2010 | Stevenson et al. |
| 2010/0217262 A1 | 8/2010 | Stevenson et al. |
| 2010/0222856 A1 | 9/2010 | Halperin et al. |
| 2010/0222857 A1 | 9/2010 | Halperin et al. |
| 2010/0280584 A1 | 11/2010 | Johnson et al. |
| 2010/0321163 A1 | 12/2010 | Stevenson |
| 2010/0324639 A1 | 12/2010 | Stevenson et al. |
| 2011/0001610 A1 | 1/2011 | Stevenson et al. |
| 2011/0022140 A1 | 1/2011 | Stevenson et al. |
| 2011/0040343 A1 | 2/2011 | Johnson et al. |
| 2011/0054582 A1 | 3/2011 | Dabney et al. |

FOREIGN PATENT DOCUMENTS

| | | |
|---|---|---|
| WO | 2005114685 A1 | 12/2005 |
| WO | 2006031317 | 3/2006 |
| WO | 2007102893 A2 | 9/2007 |
| WO | 2007117302 A2 | 10/2007 |
| WO | 2007145671 A2 | 12/2007 |

OTHER PUBLICATIONS

International Search Report and Written Opinion for International Patent Application No. PCT/US2006/41109 mailed May 3, 2007.

Baker et al., "Neurostimulation systems: assessment of magnetic field interactions associated with 1.5- and 3-Tesla MR systems," J Magn Reson Imaging, vol. 21, No. 1, 2005, pp. 72-77.

Bhidayashiri et al., "Bilateral neurostimulation systems used for deep brain stimulation: in vitro study of MRI-related heating at 1.5 T and implications for clinical imaging of the brain," Magn Reson Imaging, vol. 23, No. 4, 2005, pp. 549-555.

Rezai et al., "Neurostimulators: potential for excessive heating of deep brain stimulation electrodes during magnetic resonance imaging," J Magn Reson Imaging, vol. 14, No. 4, 2001, pp. 488-489.

Chou et al., "RF heating of implanted spinal fusion stimulator during magnetic resonance imaging," IEEE Trans Biomed Eng, vol. 44, No. 5, 1997, pp. 367-373.

Luechinger et al., "In vivo heating of pacemaker leads during magnetic resonance imaging," Eur Heart J, vol. 26, No. 4, 2005, pp. 376-383.

Martin, "Can cardiac pacemakers and magnetic resonance imaging systems co-exist?" Eur Heart J, vol. 26, No. 4, 2005, pp. 325-327.

Yoda, K., "Decoupling technique for transmit coils in NMR spectroscopy and imaging," NMR Biomed, vol. 3, No. 1, 1990, pp. 27-30.

Buchli et al., "Increased RF power absorption in MR imaging due to RF coupling between body coil and surface coil," Magn Reson Med, vol. 9, No. 1, 1989, pp. 105-112.

Ladd et al., "Reduction of resonant RF heating in intravascular catheters using coaxial chokes," Magn Reson Med, vol. 43, No. 4, 2000, pp. 615-619.

* cited by examiner

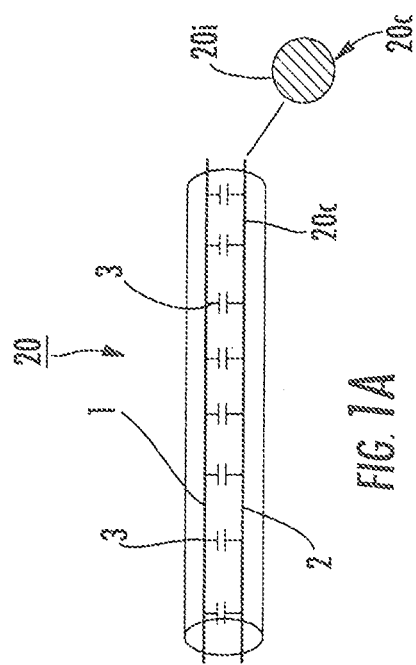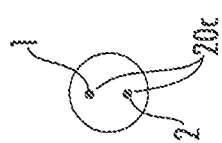
FIG. 1A
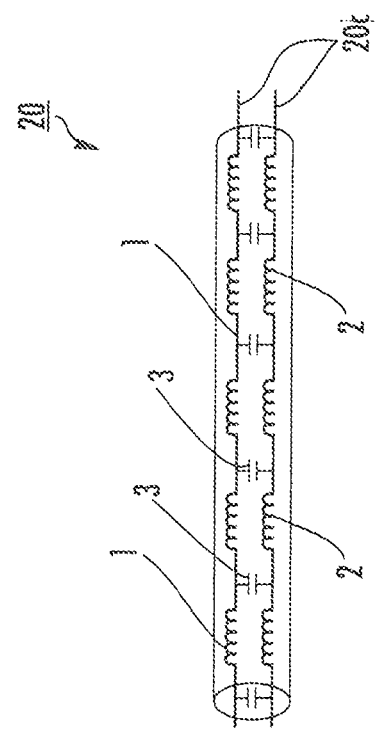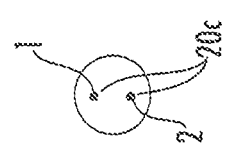
FIG. 1B

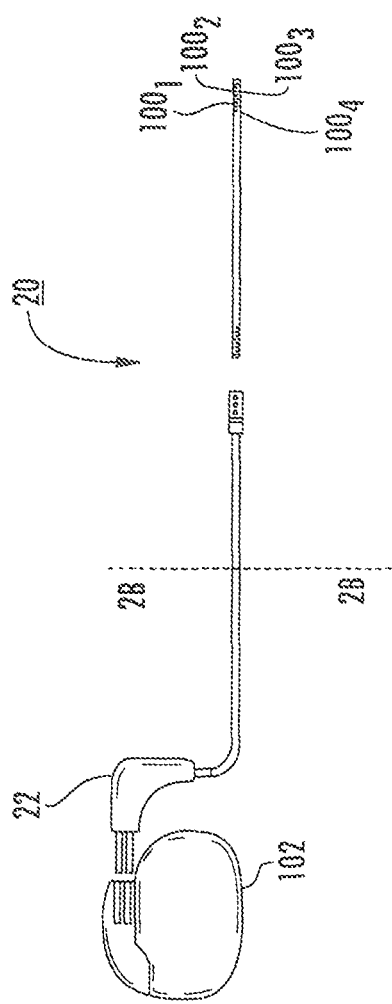
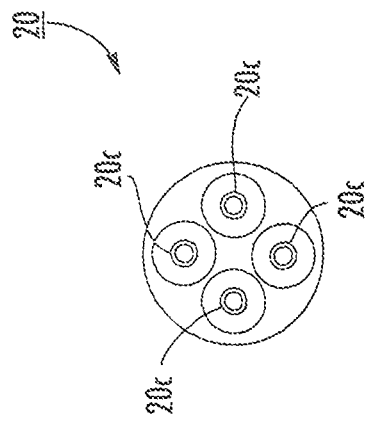
FIG. 2A
FIG. 2B

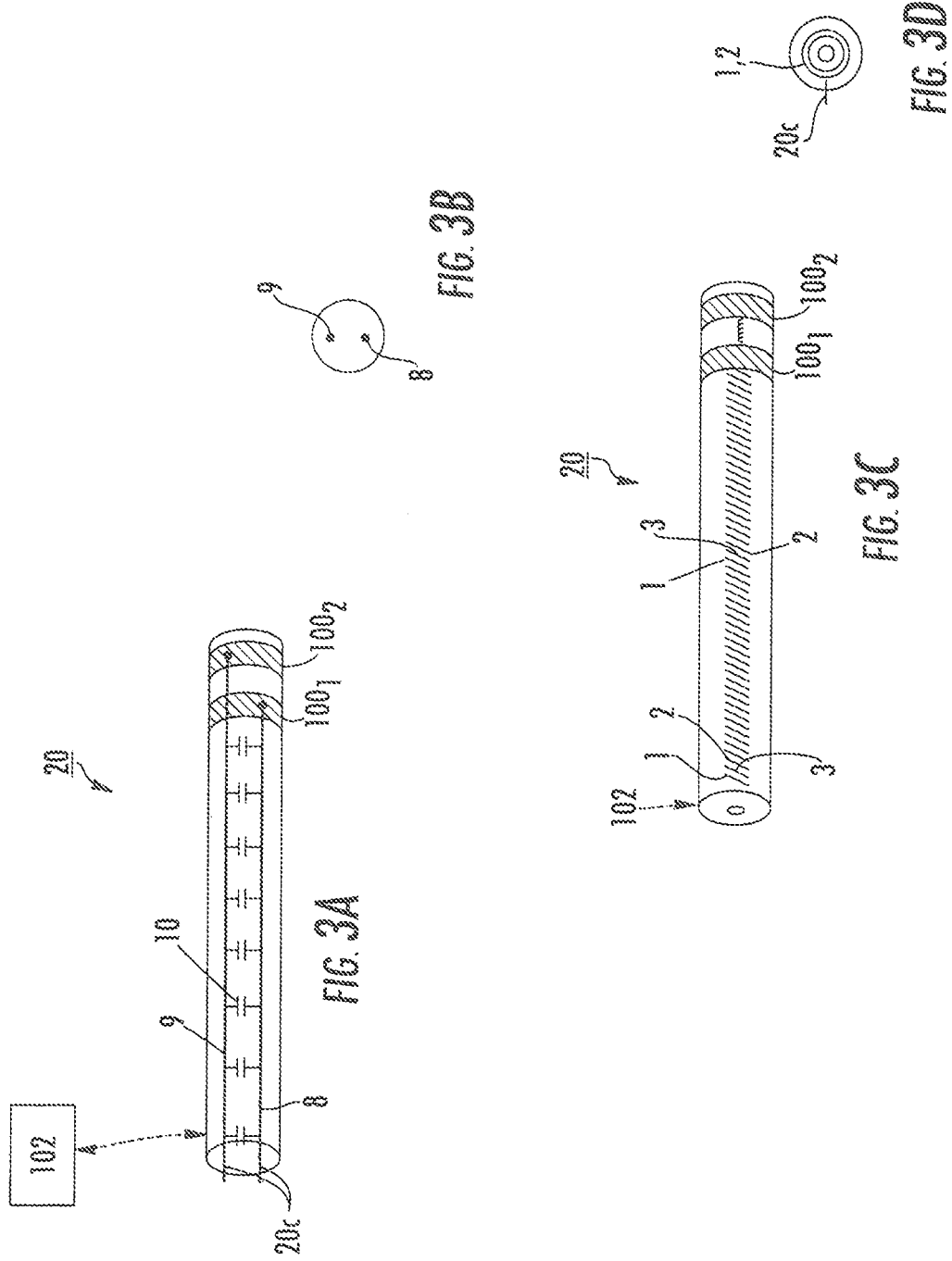

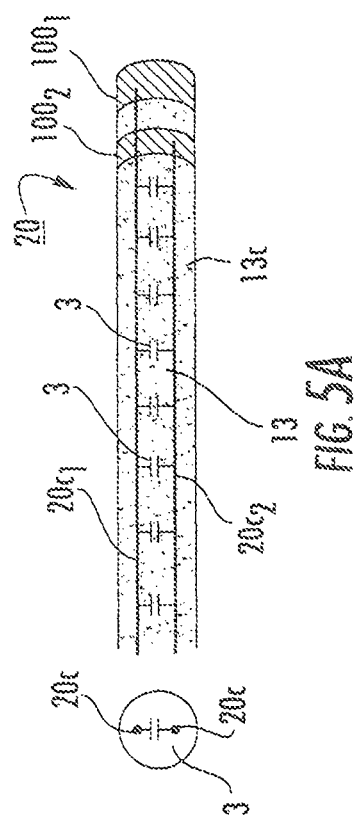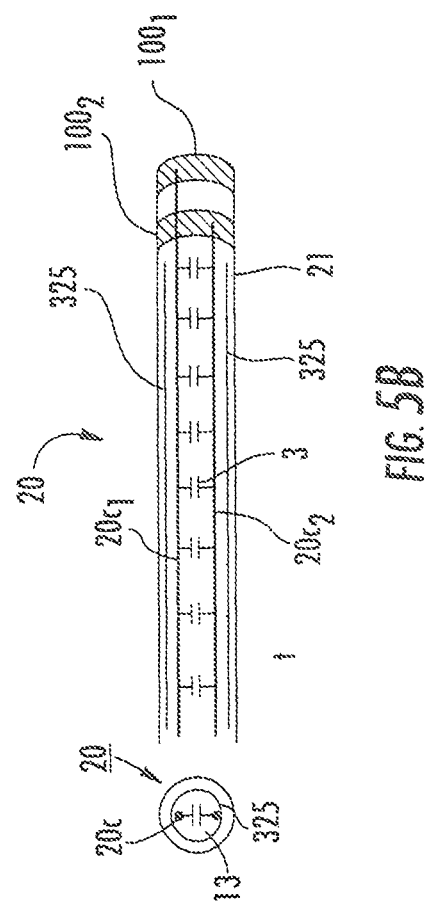

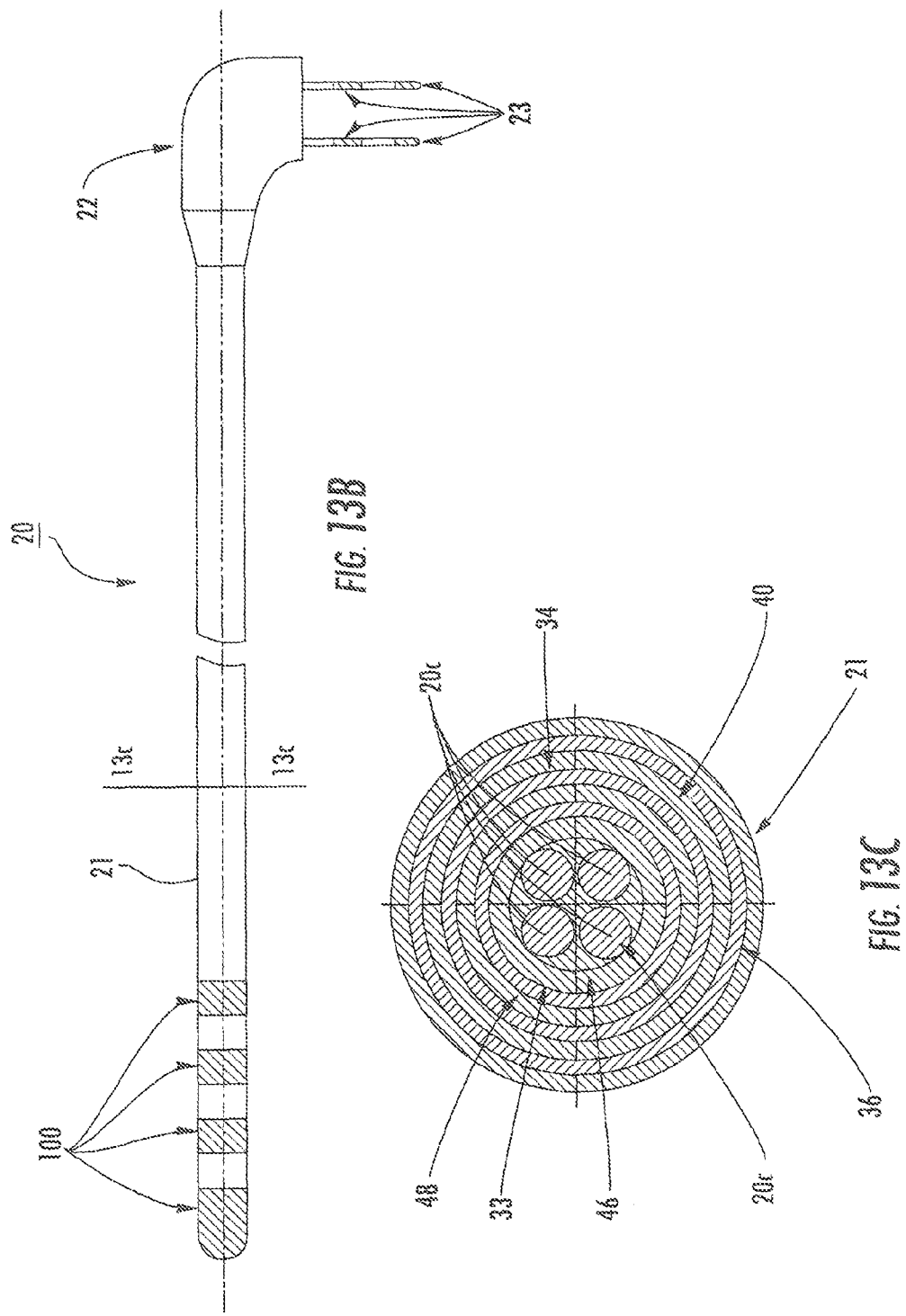

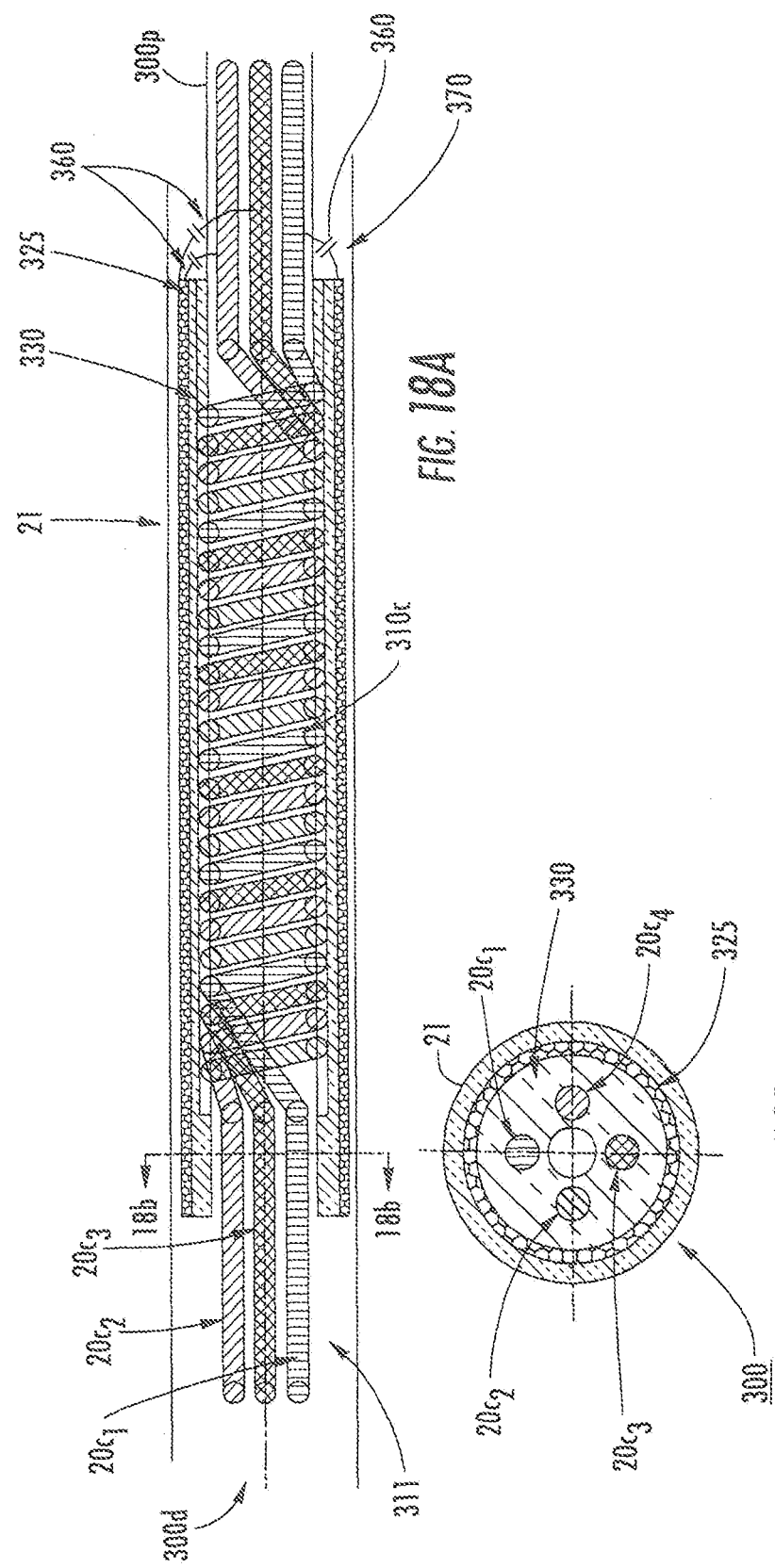

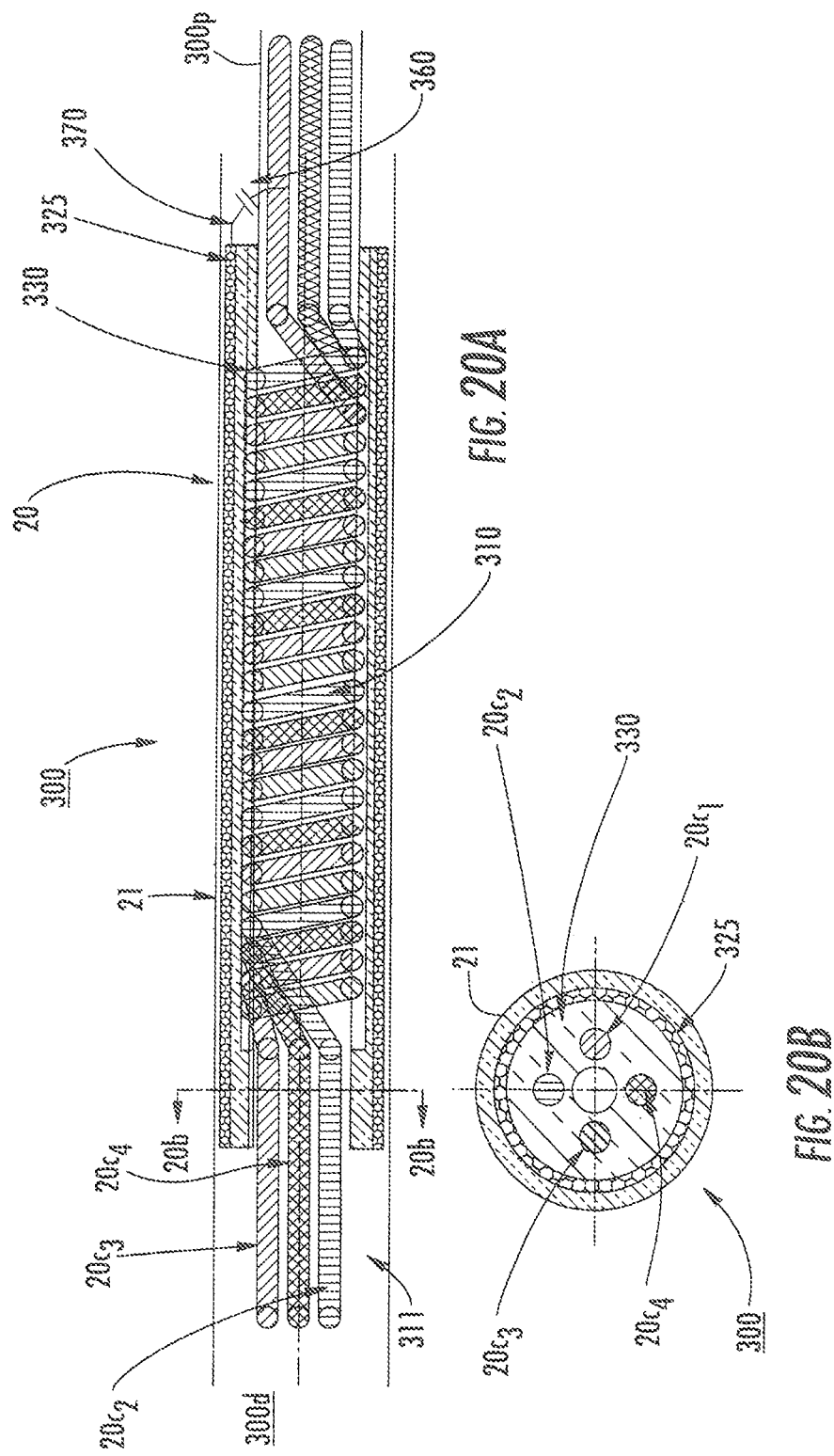

MRI-SAFE HIGH IMPEDANCE LEAD SYSTEMS

CROSS-REFERENCE TO RELATED APPLICATIONS

This patent application is a continuation of U.S. patent application Ser. No. 12/090,583, filed Sep. 5, 2008, now U.S. Pat. No. 8,055,351, issued Nov. 8, 2011, which is a 35 USC 371 national phase application of PCT/US2006/041109, filed Oct. 20, 2006, which claims the benefit of priority of U.S. Provisional Application Ser. No. 60/729,020, filed Oct. 21, 2005, the contents of which are hereby incorporated by reference as if recited in full herein.

FIELD OF THE INVENTION

The present invention relates to interventional medical leads and may be particularly suitable for MRI compatible implantable devices such as cardiac pacing devices and Deep Brain Stimulation ("DBS") and/or sympathetic nerve chain stimulation leads.

BACKGROUND OF THE INVENTION

When patients implanted with deep brain stimulation (DES) or cardiac pacing (CP) lead systems are exposed to external Radio Frequency (RF) fields, local tissue damage around the electrodes of these leads can occur as has been reported by various researchers. See, e.g., Baker et al., *Neurostimulation systems: assessment of magnetic field interactions associated with 1.5- and 3-Tesla MR systems*, J Magn Reson Imaging 2005; 21(1):72-77; Bhidayasiri et al., *Bilateral neurostimulation systems used for deep brain stimulation: in vitro study of MRI-related heating at 1.5 T and implications for clinical imaging of the brain*; Magn Reson Imaging 2005; 23(4):549-555; Rezai et al., *Neurostimulators: potential for excessive heating of deep brain stimulation electrodes during magnetic resonance imaging*. J Magn. Reson Imaging 2001; 14(4):488-489; Chou et al., *RF heating of implanted spinal fusion stimulator during magnetic resonance imaging*, IEEE Trans Biomed Eng 1997; 44(5):367-373; and Luechinger et al., *In vivo heating of pacemaker leads during magnetic resonance imaging*, Eur Heart J 2005; 26(4): 376-383; discussion 325-377.

There are several external RF sources such as, for example, RF exposure during MRI or during RF diathermy. Local tissue damage during RF diathermy procedures in patients with implanted deep brain stimulator lead systems has also been reported. RF/microwave diathermy treatments can use leads that employ an alternating current to cauterize tissue. The diathermy alternating current delivered during the therapy can be in the range of between about 1 KHz-350 MHz (believed to be typically at about 27.5 MHz). In certain situations, the lead system may undesirably act as an antenna, receiving and depositing current in localized tissue where the leads are exposed, thereby potentially increasing the specific absorption rate (SAR) (a way of measuring the quantity of radiofrequency (RF) energy that is absorbed by the body).

RF heating of tissue in close proximity to long conductors (such as metallic wires) in an MRI environment has also been reported in literature. Local tissue damage can be caused by RF deposition in the tissue that is in close proximity to the linear conductors or electrodes of the lead system, when patients with implanted leads or interventional devices are placed in an external RF field. This RF heating mechanism may be explained as follows. During an MRI scan, the transmit RF field creates a voltage along the long linear conductors (individual or part of any interventional device) or the conductors/filers of the DBS and cardiac pacing lead systems. Currents are then created through the conductors and into the surrounding tissue. Where the current emerges from the distal tip of the device (or adjacent to the electrode in the case of an implantable lead), it can be concentrated and can cause heating and subsequent tissue damage.

In view of the foregoing, there remains a need for alternative medical lead configurations.

SUMMARY OF EMBODIMENTS OF THE INVENTION

Some embodiments of the present invention provide therapeutic lead systems that can exhibit high impedance during exposure to RF (high frequencies).

The lead systems can be used with interventional devices and may be acutely placed in vivo or chronically implantable and can include one or more stimulating, ablating and/or recording electrode. The lead systems may be particularly suitable for implantable lead systems for IPGs (implantable pulse generators), cardiac defibrillators, cardiac pacing (CP), neurostimulation (peripheral, deep brain, or spinal), EP catheters, guidewires, and the like, for leads used in heat-sensitive regions in the body.

The lead systems may be implantable, MRI compatible multi-purpose lead systems with at least one stimulating/pacing electrode and may optionally be configured to provide an internal MRI receive antenna.

In some embodiments, the lead systems can include a plurality of high impedance sections or segments spaced along the length of the lead. The high impedance sections can be configured as RF traps that inhibit flow of induced RF current at the high impedance frequency/frequencies, whereby current is inhibited from heating tissue adjacent to one or more electrodes, thus reducing the likelihood of and/or preventing RF-current induced tissue damage. The RF traps can be configured to allow physiological and stimulation signals to pass through (typically in the kHz range). Thus, the RF trap can trap only the high frequencies of interest to which the traps are tuned.

Embodiments of the invention describe different methods of creating high impedance RF traps using the components of an implantable lead system or a medical device. The RF traps may be incorporated in long metallic components to render them safe to use in an MRI environment.

The lead systems may include supplemental high impedance circuits for the shield in combination with the high impedance configurations for conductors.

Some embodiments are directed to interventional devices and/or implant devices comprising metal or metallic components.

In particular embodiments, a lead can be a relatively long implantable lead having a length in the body of greater than 10 cm. The at least one electrode can be a plurality of electrodes with at least one being a recording and/or a recording and stimulating and/or ablating electrode.

Some embodiments are directed to MRI/RF compatible medical interventional devices. The devices include an implantable elongate lead system having at least a first and a second electrode, each associated with a respective first and second axially extending conductor. A plurality of axially spaced apart capacitors are disposed between the first and second axially extending conductor along at least major portion of a length of the lead system to define, a plurality of high impedance circuit segments whereby the lead system has a high impedance over a target range of (typically a high range) of radiofrequencies and a low impedance over another range of low electromagnetic frequencies (such as audio-frequencies or frequencies in the kHz or lower ranges, including DC at around 0 Hz).

The high impedance circuit segments may be configured to inhibit RF transmission along the lead system during exposure to RF associated with a high-field magnet MRI system.

Other embodiments are directed to MRI compatible device/lead systems that include: (a) an implantable lead system elongate lead having at least a first and a second electrode, each associated with a respective first and second axially extending conductor; and (b) a high impedance surface band gap structure disposed about the first and second conductors.

The surface band gap structure may include a primary shield and secondary and tertiary segmented shields which are intermittently connected to the primary shield, whereby the high impedance surface reduces or blocks RF propagation.

Other embodiments are directed to an MRI compatible device that includes: (a) an implantable lead system elongate lead having at least a first and a second electrode, each associated with a respective first and second axially extending conductor, wherein a plurality of spaced apart capacitors are disposed between the first and second axially extending conductors along at least major portion of a length of the lead system to define a plurality of high impedance circuit segments; and (b) a high impedance band gap surface formed along at least a major length of the lead system. The lead system has a high impedance at a high range of radiofrequencies and a low impedance at a low range of frequencies.

Still other embodiments are directed to MRI compatible implantable pulse generators (IPG). The IPG's include: (a) an implantable housing; (b) a high impedance decoupling circuit disposed in the housing; (c) at least one implantable lead in communication with the decoupling circuit and configured with a length that extends from the housing to a target treatment site; (d) at least one implantable electrode in communication with the lead; and (e) a controller in the implantable housing, the controller configured to selectively activate the decoupling circuit to provide a high impedance to the lead at high radiofrequencies and a low impedance at a low radiofrequencies.

In particular embodiments, the controller is remotely controllable to activate the decoupling circuit to provide the high impedance.

The high impedance circuits and/or circuit segments may comprise inductors. Inductors and capacitors can be formed form conducting leads and a dielectric substrate and can be configured to reduce, block or inhibit RF transmission along the lead system during exposure to RF associated with a high-field magnet MRI system, while permitting passage of low frequency physiologic signals, treatments and/or stimuli.

The lead may be a flexible lead and the at least one electrode can be a plurality of spaced apart electrodes. The lead can include a plurality of conductors held in a core of the lead, a respective one for each electrode.

Some embodiments are directed to MRI safe lead systems that include: (a) an elongate flexible body with at least one conductor; (b) at least one electrode in communication with the at least one conductive lead; and (c) a plurality of high impedance segments axially spaced apart along a length of the lead system. The at least one conductive lead has a plurality of axially spaced apart coiled segments and a plurality of linear segments residing between adjacent coiled segments. The high impedance segments include: (a) a coiled conductive lead segment defining an inductor; (b) a dielectric over the coiled conductive lead segment; (c) a conductive shield over the dielectric with the dielectric residing between the inductor and the conductive shield, wherein the conductive lead is electrically coupled to the shield at a proximal end portion of the coiled segment; and (d) a capacitor at a distal end of the coiled conductive lead segment electrically connecting the conductive lead and the shield. The high impedance segments are configured to provide an impedance that is greater than about 450 Ohms at a target RF frequency associated with an MRI system.

Some embodiments are directed to MRI-safe lead systems that include: (a) an elongate flexible body with a plurality of conductors, the body having distal and proximal portions, the conductors each having a plurality of axially spaced apart coiled segments, each coiled segment defining an inductor; (b) at least one electrode residing at the distal portion of the flexible body in communication with at least one of the conductors; and (c) a plurality of high impedance segments axially spaced apart along a length of the lead. The high impedance segments include: (i) a plurality of coiled conductor segments residing at a common axially extending segment of the flexible body, at least one coiled lead segment for each of the conductors; (ii) a dielectric insulator covering the plurality of coiled conductor segments at the common axial segment; and (iii) a conductive shield at the common axial segment disposed over the dielectric insulator with the dielectric insulator residing between the coiled segments and the conductive shield. A single one of the plurality of conductors is electrically coupled to the conductive shield at a proximal end portion of the common axial segment.

Some embodiments are directed to MRI-safe lead systems that include an elongate flexible body with a plurality of conductors and at least one high impedance segment with opposing proximal and distal portions. The at least one high impedance segment is configured so that at least one of the conductors has (a) a first individually coiled segment that is proximate to but axially apart from the coiled segments of different leads, and (b) a second coiled segment that is co-wound with at least one other conductor coiled segment. A conductive shield resides over the first lead first and second coiled segments and an insulating material resides between the shield and the first and second coiled segments. The at least one lead with the individual and co-wound coiled segments is in electrical communication with the shield at a proximal portion of the high impedance segment.

Other systems, methods, and/or computer program products according to embodiments of the invention will be or become apparent to one with skill in the art upon review of the following drawings and detailed description. It is intended that all such additional systems, methods, and/or computer program products be included within this description, be within the scope of the present invention, and be protected by the accompanying claims.

BRIEF DESCRIPTION OF THE DRAWINGS

FIGS. 1A and 1B are schematic illustrations of high impedance lead systems according to embodiments of the present invention.

FIGS. 2A-2B are schematic illustrations of examples of multi-electrode lead systems with an IPG, which may include high impedance circuits or segments to provide a high impedance operation at selected RF frequencies according to embodiments of the present invention.

FIGS. 3A and 3C are schematic diagrams that illustrate a lead system with electrodes and capacitors disposed therealong according to embodiments of the present invention. FIG. 3A illustrates a linear system and FIG. 3C illustrates a wound/coiled system.

FIGS. 3B and 3D are schematic cross-sectional views of the systems shown in FIGS. 3A and 3B, respectively.

FIGS. 5A and 5B are schematic diagrams of other multi-electrode high impedance leads according to embodiments of the present invention.

FIG. 13B is a section view of the lead system shown in FIG. 13A illustrating shielding and conductor configurations according to embodiments of the present invention.

FIG. 13C is a cross-sectional view of the lead system shown in FIG. 13B.

FIG. 18A is a partial cutaway side view of a multi-lead system with an RF trap having co-wound conductors/filars according to some embodiments of the invention.

FIG. 18B is a cross-section view taken along lines 18B-18B in FIG. 18A.

FIG. 20A is a partial cutaway side view of a multi-lead system with an RF trap having co-wound conductors/filers with less than all the leads/conductors in electrical contact with the shield according to some embodiments of the invention.

FIG. 20B is a cross-section view taken along lines 20B-20B in FIG. 20A.

DETAILED DESCRIPTION OF EMBODIMENTS OF THE INVENTION

Figure 4:
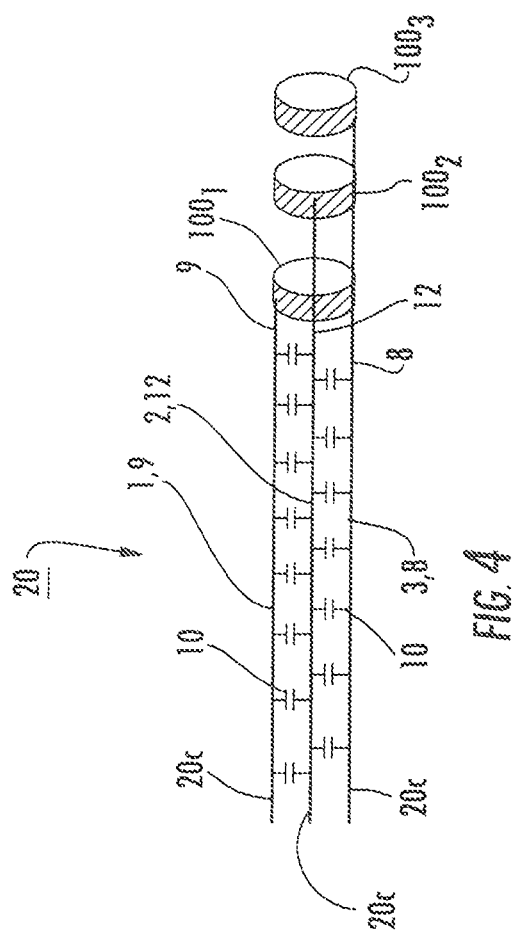
FIG. 4 is a schematic diagram that illustrates three conductors, three electrodes and capacitors disposed between conductor pairs according to embodiments of the present invention.

The present invention will now be described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. It will be appreciated that although discussed with respect to a certain embodiment, features or operation of one lead system embodiment can apply to others.

In the drawings, the thickness of lines, layers, features, components and/or regions may be exaggerated for clarity and broken lines illustrate optional features or operations, unless specified otherwise. In addition, the sequence of operations (or steps) is not limited to the order presented in the claims unless specifically indicated otherwise. It will be understood that when a feature, such as a layer, region or substrate, is referred to as being "on" another feature or element, it can be directly on the other element or intervening elements may also be present. In contrast, when an element is referred to as being "directly on" another feature or element, there are no intervening elements present. It will also be understood that, when a feature or element is referred to as being "connected" or "coupled" to another feature or element, it can be directly connected to the other element or intervening elements may be present. In contrast, when a feature or element is referred to as being "directly connected" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and this specification and should not be interpreted in an idealized or overly formal sense unless expressly so defined herein.

The term "high radiofrequency" or "high RF" refers to RF frequencies that are at or above about 1 MHz, and includes radiofrequencies in the range of about 1 MHz to about 256 MHz. Embodiments of the present invention configure devices so as to have high impedance circuit segments or a high impedance circuit at high RF and low impedance circuit segments or circuit at DC or low frequency (at a kHz or less frequency or frequency range), i.e., at frequencies used for treatment such as stimulation or ablation. For example, for 1.5 T, 3.0 T and 6.0 T systems, the respective frequencies are 64 MHz, 128 MHz and 256 MHz. The frequencies of the different MRI systems are well known to those of skill in the art. The devices can be configured to have high impedance at several of the radiofrequencies associated with high-field magnet MRI systems, such as systems with magnets above about 1.0 T, such as about 1.0 T, 1.5 T, 2.0 T, 3.0 T, 4.0 T, 5.0 T, 6.0 T and 9.0 T, typically between about 1 T to 15 T.

The term "high impedance" means an impedance sufficiently high to inhibit, block or eliminate flow of RF-induced current at a target frequency range(s). The impedance has an associated resistance and reactance as is well known to those of skill in the art. Some embodiments provide an impedance of at least about 300 Ohms, typically between about 400 Ohms to about 600 Ohms, such as between about 450 Ohms to about 500 Ohms, while other embodiments provide an impedance of between about 500 Ohms to about 1000 Ohms. Embodiments of the invention configure lead systems that provide sufficiently high-impedance at frequencies associated with a plurality of different conventional and future magnetic field strengths of MRI systems, such as at least two of 1.5 T, 2.0 T, 2.5 T, 3.0 T, 9.0 T, and the like, allow for safe use in those environments (future and reverse standard MRI system compatibility).

The term "tuned" means that a parallel resonant circuit with inductive and capacitive characteristics defined by certain components and configurations has a high impedance at one or more target frequencies, typically including one or more MRI operating frequencies.

The term "coiled segment" refers to a conductive lead (trace, wire or filar) that has a coiled configuration. The term "co-wound segments" means that the affected leads, conductors, wires and/or filars can be substantially concentrically coiled at different radii, one above the other, or concentrically coiled closely spaced at substantially the same diameter. The term "co-wound" is used to describe structure and is not limiting to how the structure is formed (i.e., the coiled segments are not required to be wound concurrently or together, but may be so formed). The terms "conductive element", "conductive lead" and "conductors" are used interchangeably and refer to a conductive path that connects target components (such as, for example, a stimulation source and an electrode) and can include one or combinations of a metallic trace, a wire, a flex circuit, a filar(s), or other conductive configuration. As such, the conductors or conductive elements include long linear and/or non-linear conductors that can be formed with one or more of discrete wires, flex circuits, filars (bi, quadra or other winding), or by plating, etching, deposition, or other fabrication methods for forming conductive electrical paths.

Embodiments of the present invention can be configured to for any desired internal region of the body or object. The object can be any object, and may be particularly suitable for animal and/or human subjects. Some embodiments can be sized and configured for brain stimulation, typically deep brain stimulation. Some embodiments can be configured to stimulate a desired region of the sympathetic nerve chain and/or the spinal cord. Some lead or implantable devices can be configured for cardiac intervention. Other embodiments may be directed to other anatomical structures, organs or features including deep tissue, lumens, and the like. For example, the systems of the present invention may be configured for treatment of gastrointestinal, urinary, or other body regions. Some embodiments provide devices configured for intraluminal or intratissue penetration. Some embodiments provide devices for acute or chronic implantation.

Examples of known stimulation treatments and/or target body regions are described in U.S. Pat. Nos. 6,708,064; 6,438,423; 6,356,786; 6,526,318; 6,405,079; 6,167,311; 6539,263; 6,609,030 and 6,050,992, the contents of which are hereby incorporated by reference as if recited in full herein.

Generally stated, the extent to which the lead system or the long conductor couples with the external RF is a function of length of the lead system or the conductor, the insulation thickness over it and its arrangement in the RF field e.g. looping, etc. Typically, lengths shorter than quarter wavelength (at the applied RF frequency) do not couple with the external RF fields, displaying reduced RF deposition and lower local temperature rise in tissue adjacent to them. Also, typically, increasing the insulation thickness can reduce the coupling and RF deposition in the adjacent tissue.

Long wires, conductors and lead systems couple to external RF to different extents at different frequencies. The extent of RF deposition in the tissue depends on the extent of resonation, i.e., the coupling at that frequency. Linear conductors/ wires act as linear antennas. Lead systems which have more than one long conductor act as linear antennas, where each individual conductor acts as an antenna and two or more conductors in combination with each other act as antennas too. This creates a RF coupling pattern having the lead system couple at multiple/different frequencies. DBS and cardiac pacing leads may comprise about 8 (and may include more or less) long conductors and electrodes. In particular embodiments, one, some or all of the conductors can act as antennas individually and in combination with each other.

Internal and external imaging coils used in MRI can be decoupled during RF transmit by the scanner. This can inhibit local heat deposition in the tissue adjacent to the coils. The decoupling mechanism can create a high impedance circuit so that these coils do not couple with the transmitted RF, thus eliminating any tissue damage. See, Yoda K., *Decoupling technique for transmit coils in NMR spectroscopy and imaging*, NMR Biomed 1990; 3(1):27-30; and Buchli et al., *Increased RF power absorption in MR imaging due to RF coupling between body coil and surface coil*, Magn Reson Med 1989; 9(1):105-112.

Similarly, standing wave formation on long coaxial cables may be attenuated by incorporating balun circuits or RF chokes at various locations on the shield of coaxial cables. See, Atalar et al., U.S. Pat. No. 6,284,971, entitled, Enhanced Safety Coaxial Cables, the contents of which is hereby incorporated by reference as if recited in full herein. See also, Ladd et al., *Reduction of resonant RF heating in intravascular catheters using coaxial chokes*, Magn Reson Med 2000; 43(4): 615-619. See also, PCT Application Serial No., PCT/ US2005/028116, filed Aug. 9, 2005, entitled, Implantable MRI Compatible Stimulation Leads and Antennas and Related Systems and Methods, the contents of which are hereby incorporated by reference as if recited in full herein. Generally stated, this application describes incorporating RF chokes on DBS and CP lead systems.

Shielding linear conductors can inhibit RF deposition on them. This shielding can be continuous, discontinuous, or may be achieved by multiple methods, to list a few, e.g., insulating conductors with polymers filled with conducting metals doped for conductivity.

Referring now to the figures, in some embodiments as shown in FIGS. 1A and 1B, a high impedance lead assembly 20 can employ at least one conductor 20c, shown as two conductors 1, 2 which may be coiled (FIG. 1B) and/or reside parallel (FIG. 1A) to each other, or be configured with combinations of both, and that are operational over a relatively wide range of frequencies. These long conductors $20c$ can have a metal core and are typically insulated from each other along their length and may be surrounded by a polymeric dielectric $20i$. At intermediate locations, the two conductors $1, 2$ can be connected by capacitors $3$. The combination of the length of the conductors $1$ and $2$ (which can also form inductors) and the capacitors $3$ can be configured to create a high impedance circuit(s). This circuit can be configured so that it does not tune to a target range of RF frequencies, including for example, frequencies ranging from about 1 MHz to 250 MHz, creating high impedance circuit segments, thus reducing the extent of coupling in this frequency range. In operation, the circuit has high impedance to high RF, but has low resistance to DC, or low frequency RF (KHz), which is the stimulation frequency. This principle may be applied to designing RF/MRI-safe devices and/or lead systems for CP leads, DBS leads, spinal cord stimulation leads, etc.

The capacitors $3$ can be regularly spaced or irregularly spaced. The capacitors $3$ may have the same or different capacitance from each other.

Lead systems $20$ can comprise a plurality of electrodes and conductors, such as between about 2 to about 10 conductors, typically at least about 4. In some embodiments, the lead systems can include about 8 conductors. The conductor axial lengths (linear and/or coiled) can range from about 10 to 200 cm, with a thin insulator layer on the conductors and with a polymeric dielectric insulator layer over it.

Design of conventional known lead systems with multiple electrodes $100_1$-$100_4$ and conductors $20c$ are shown in FIGS. 2A-2B. See also, U.S. Patent Application Publication No. 2005/0222647, the contents of which are hereby incorporated by reference as if recited in full herein.

Referring to FIGS. 3A and 3B, at a distal end portion of the lead system $20$, the conductors $20c$ can be connected to electrodes $100_1$, $100_2$, which, in position, can be in contact with target tissue. The conductors $20c$ run along the length of the lead system and are terminated by connecting to electrodes $100_1$ and $100_2$ at the distal end. At the proximal end these conductors are connected to the pulse generator (IPG). The conductors are typically made of stainless steel or other conducting non-ferromagnetic material. The concepts described herein can be implemented in creating a high impedance lead system for multi-electrode leads such as those shown in FIGS. 2A-2E.

In some embodiments, as shown in FIG. 3A, two (straight/linear) parallel conductors $8$ and $9$ are connected to each other at intermediate locations by capacitors $10$ along the length of the lead system to form high impedance sections. The capacitors $10$ can be semiconductor-based discrete products or can be otherwise provided, such as using coatings of metal oxides, e.g. tantalum oxide, and the like at discrete certain locations so as to connect the two conductors $8, 9$ at desired locations.

FIG. 3B, similar to FIG. 3A, illustrates two parallel conductors but as wound conductors $1, 2$ with spaced capacitors $3$ in communication therewith and two respective electrodes $100_1$, $100_2$.

In embodiments that employ more than two conductors $20c$, more than one high impedance circuit can be formed with different conductor pairs. For example, as shown in FIG. 4, where there are three electrodes $100_1$, $100_2$, $100_3$ and three conductors $20c$, labeled as elements, $8, 9,$ and $12$, respective capacitors $10$ can be disposed between conductor pairs ($8, 12$ or $12, 9$, as shown). Also, one conductor $20c$ may be used in combination with two conductors to form two separate high impedance circuits.

In some embodiments, the lead systems $20$ can conduct DC or a low frequency AC (KHz), typical of stimulation current. The conductors $20c$ may be made of any suitable (MRI compatible and/or non-ferromagnetic) conducting material and/or metal, e.g., Nitinol, Cobalt-Chromium alloy, MP35N alloy, gold, silver, platinum, platinum-iridium alloy, stainless steel, copper and other non-ferromagnetic materials, which will not cause a susceptibility artifact in MRI or magnetically react to the magnetic field in an MRI scanner environment. DC conductivity is a bulk phenomenon and RF conductivity is a skin depth phenomenon. The RF conductivity of the lead system may be reduced by using composite wire (a conductor or wire formed of a combination of different conductive materials) such as by using a resistive metal such as tungsten, MP35N or Nitinol wire on the outside and with a conductive core formed of gold, silver or copper or other metals. This may reduce RF transmission along the length of the lead system, thus reducing the amount of RF that may be deposited in the tissue. Further, these leads made of composite wires (with a resistive outer layer and conductive core) can have an insulator coating on the outer surface and may be connected by capacitors to form high impedance RF circuits along the length of the lead system as described above with respect to FIGS. 1-4.

FIGS. 5A and 5B illustrate lead systems formed with high impedance segments of two or more insulated conductors $20c$ with any single conductor and/or a composite conductor structure having a polymeric layer $13$ over them. As shown, the leads may be further shielded by a polymeric dielectric material with metal or conductive particulates $13c$ (FIG. 5A) dispersed therein to shield/deflect external RF. In some embodiments, the polymeric dielectric or insulation $13c$ over the conductors $20c$ may be filled/dispersed or mixed with another high dielectric constant material, e.g., titanium dioxide, etc., to regulate the impedance between (two or more) conductors.

Also, or alternatively, conductive shielding $325$ as a continuous or discontinuous conductor layer (braided, coated, etc) may be applied over the conductors $20c$ of the lead system as shown in FIG. 5B. An insulating polymeric material $13$ may reside between the conductors $20c_1$, $20c_2$ and the shield $325$. A polymer outer layer $21$ may encase the lead system $20$.

Figure 14:
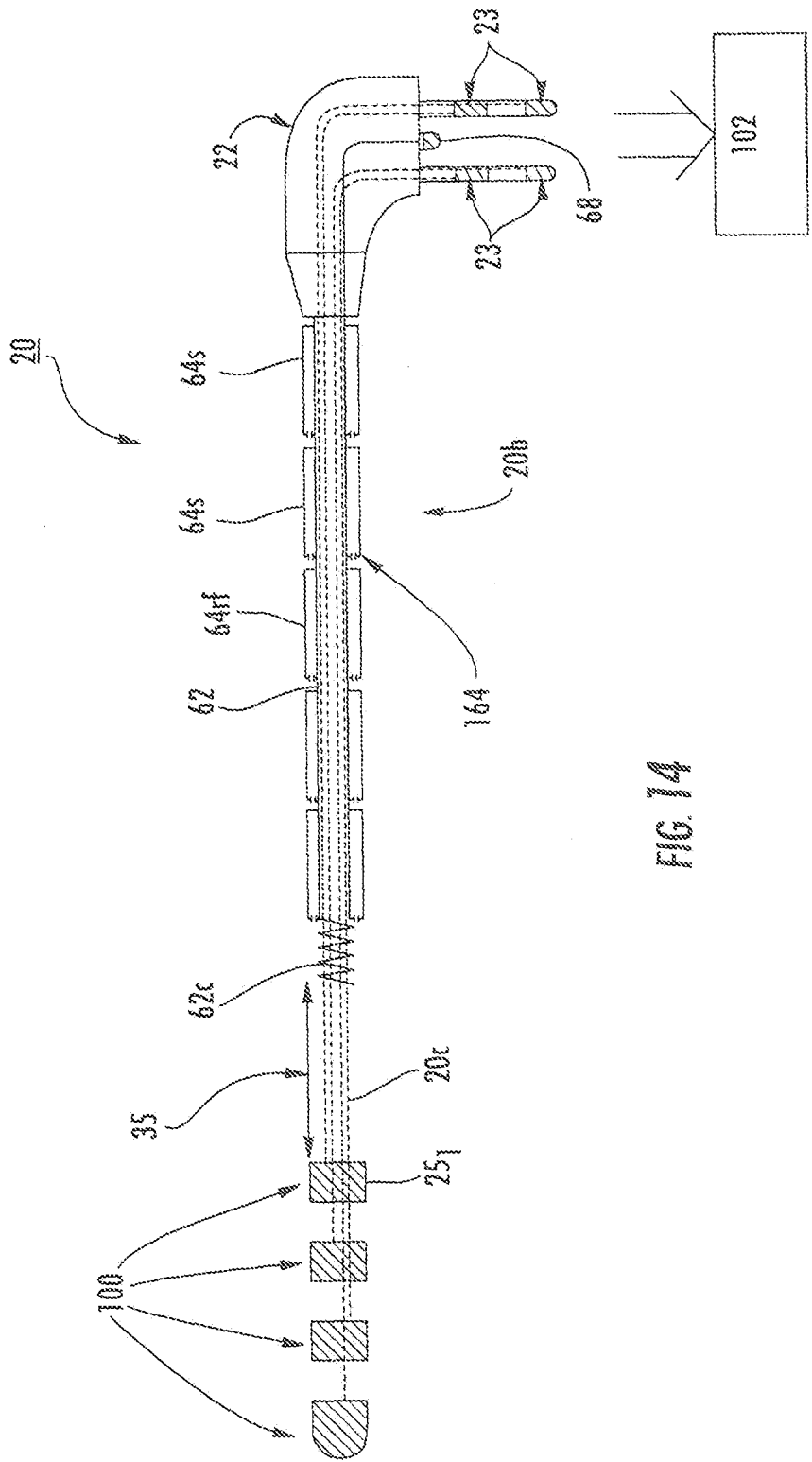
FIG. 14 is a schematic illustration of a lead system with RF chokes that may be combined with one or more of the high impedance configurations shown and/or described herein according to embodiments of the present invention.

In some embodiments, as shown in FIG. 14, RF chokes $64rf$, as described in PCT Application Serial No., PCT/US2005/028116, filed Aug. 9, 2005, entitled, Implantable MRI Compatible Stimulation Leads and Antennas and Related Systems and Methods, may be incorporated over these high impedance segments or leads to further prevent formation of standing RF waves.

Figure 6:
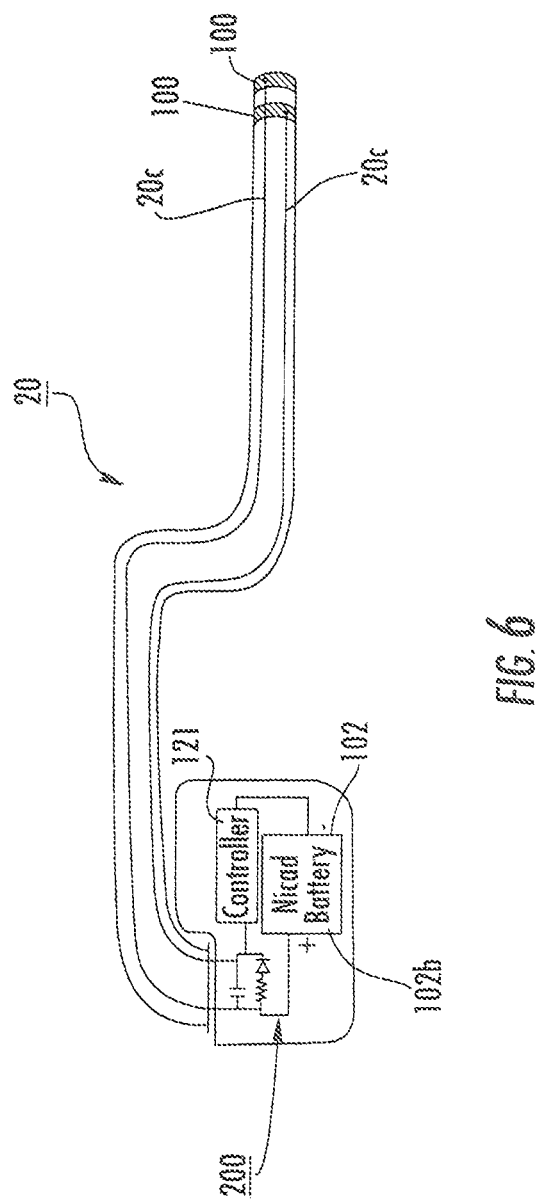
FIG. 6 is a schematic illustration of an implantable pulse generator with a high impedance operation according to embodiments of the present invention.

In some embodiments, as shown in FIG. 6, an IPG $102$ can have a lead system $20$ with multiple conductors $20c$ that connect distal electrodes $100$. The IPG may optionally include a decoupling circuit $200$ which can be incorporated in an implanted housing of the IPG $102$ and/or in a connector or portion of the IPG lead assembly (a connector or end portion of the lead assembly rather than the housing itself). The IPG $102$ can include a power source $102b$, such as a battery. The circuit $200$ can be in communication with a digital controller $121$ that can programmatically activate the circuit $200$ (and/or deactivate the circuit $200$). The lead system $20$ may optionally be arranged as an antenna described earlier with two or more capacitor sets per antenna.

Implantable IPGs can be used with other lead system configurations (see, e.g., FIGS. 15-22). The lead system can be transformed to a high impedance lead (and/or antenna) by activating the decoupling circuit 200 to a short circuit, before an MRI scan or exposure to external RF. This activation can create a high impedance circuit with the capacitors and inductor assembly in the lead body making the lead electrically invisible to the external RF thus reducing coupling with the RF. The decoupling may comprise a single or multiple circuits tuned to different frequencies and can be programmed to be activated accordingly. The activation and/or adjustment to different RF frequency and/or deactivation can be carried out by a wireless command sent to the IPG. The activation may be carried out internally (automatically) in response to detection of an RF signal.

Some lead systems 20 of the instant invention can be configured so that one or more conductors behave as inductors or comprise inductive components. The inductors can be provided by coiled conductor (wire) segments, flexible dielectric substrates, or other inductor configurations. In some embodiments, at high frequency, capacitors can act as shorts and may not, by themselves, give sufficiently high impedance. Thus, the lead systems 20 can include inductors that cooperate with the capacitors. The leads or conductors of the systems can have high impedance at high frequency and low impedance at low frequency by configuring the conductors (wires/leads) to behave as inductors.

In some embodiments, at least one conductor 20c of the lead system 20 comprises a wound coil segment of the at least one conductor to define a coil inductor. In particular embodiments, the coil inductor may be wound to encase other another conductor(s) of the lead system. The coil inductor can be formed as substantially an entire length of a first conductor or as a smaller portion of the conductor. The capacitors can connect sections of the coil inductor and a second conductor.

Figure 7:
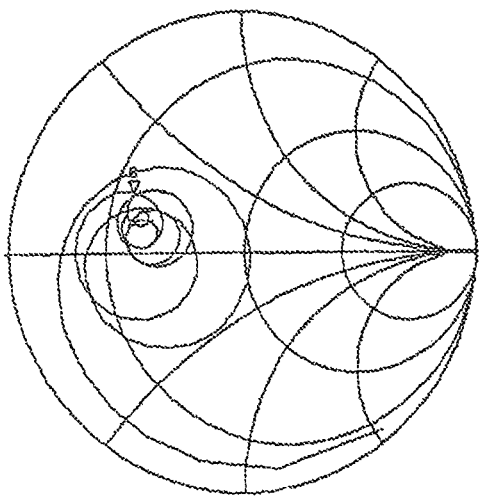
FIGS. 7 and 8 are data charts/graphs of a coiled parallel inductor pair in a frequency range of between 1-150 MHz.
Figure 8:
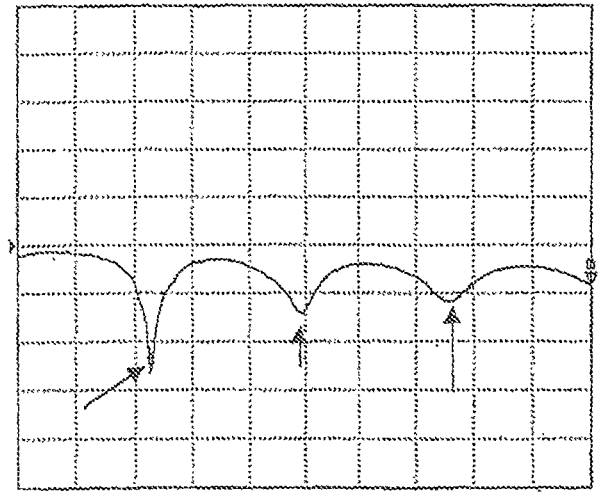

FIGS. 7 and 8 are graphs of data associated with a 12 cm long coiled inductor pair open at both ends when loaded in saline. The conductors are 32 AWG magnet wire closely wound on a 0.020 inch mandrel. The graph shows an X-axis frequency sweep from 1.0 to 150 MHz. The two-conductor assembly tunes at different frequencies to different extents as represented by the arrows in FIG. 8.

Figure 9:
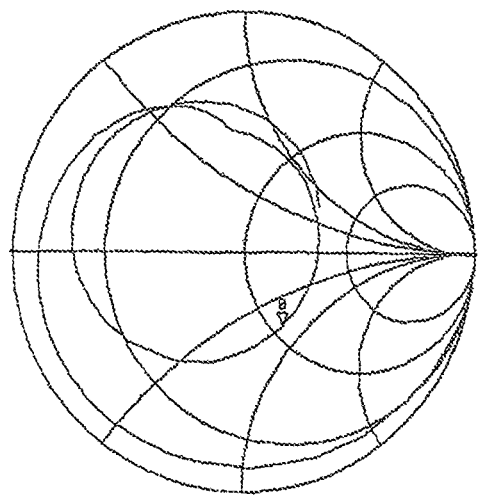
FIGS. 9 and 10 are data charts/graphs of a coiled parallel inductor similar to that shown with respect to FIGS. 7 and 8, but modified with capacitors to provide higher impedance according to embodiments of the present invention.
Figure 10:
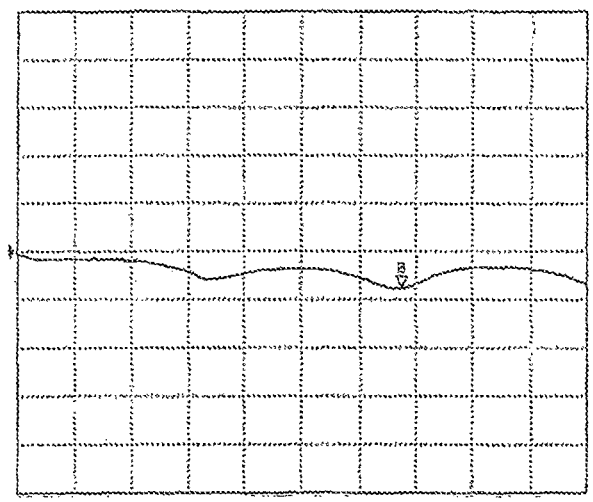

FIGS. 9 and 10 illustrate the same parallel inductors as described above (FIGS. 7 and 8) with 0.5 pF capacitors placed at about 2.5 cm apart at 5 locations. The return loss is flatter and higher than −8 db for all frequencies. It is contemplated that this loss can be further reduced (closer to zero) in an optimized design.

Figure 11:
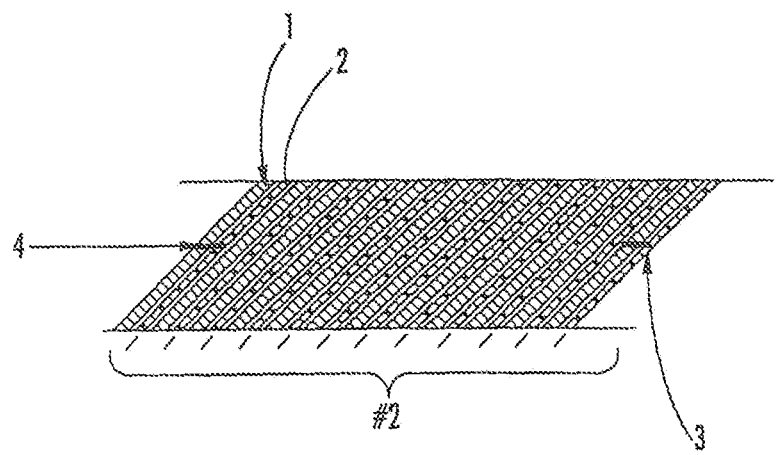
FIG. 11 is a schematic illustration of the parallel inductors and capacitors used to provide the data of FIGS. 9 and 10 according to embodiments of the present invention.

FIG. 11 is a schematic diagram of the parallel inductors with the inductor coil 1 being the wider outside strip and the inductor coil 2 being the inner strip (slightly thinner). The 0.5 pF inductors (3, 4) are shown positioned between the two inductors 1, 2 to create a high impedance system at the frequency range or ranges of interest.

Figure 12:
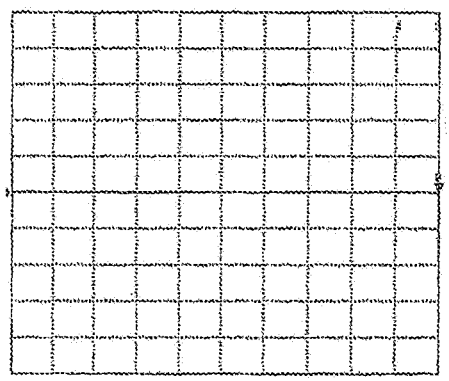
FIG. 12 is a graph of a sample loss of an open circuit for a frequency range of about 1-150 MHz.

FIG. 12 is a graph of a sample return loss of an open circuit for a frequency range of between about 1-150 MHz.

Figure 13A:
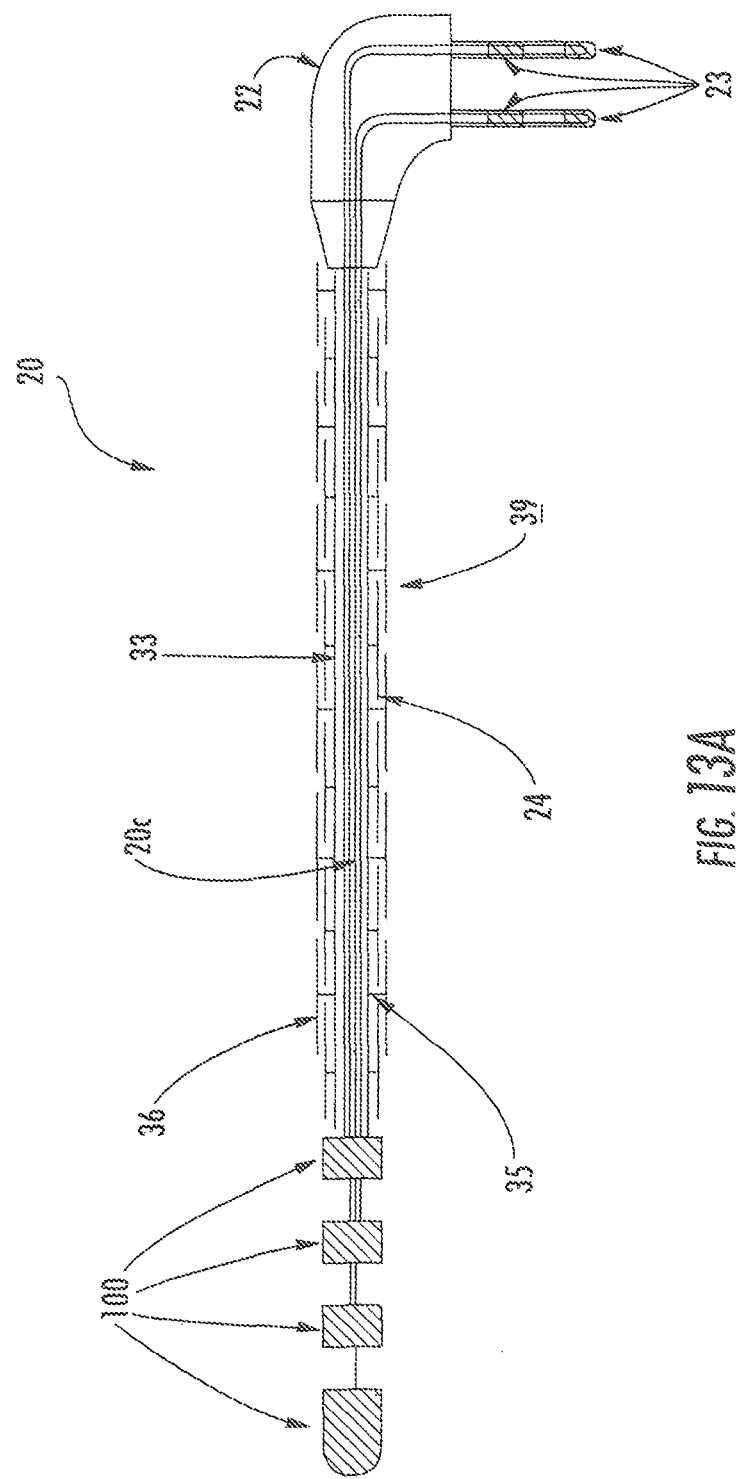
FIG. 13A is a schematic illustration of an electrode lead system with a high-impedance surface shield according to other embodiments of the present invention.

FIG. 13A illustrates another embodiment of an MRI/RF safe lead system with an IPG connector 22 and IPG electrical connections 23. As shown, the lead system 20 includes a plurality of electrodes 100, respective conductors/wires 20c, a primary shielding 33, a segmented secondary shielding 34, segments/inductors 35, and a segmented tertiary shield 36. The segments/inductors 5 connect the secondary 34 and tertiary shield 36 to the primary shield 33. The lead system 20 and/or the conductors 20c of the lead system are shielded by one or more layers of shield arrangements as shown in FIG. 13A. This creates a high impedance surface and inhibits RF coupling of the lead system and any formation and/or transmission of a standing wave. This may be defined as a "3-D RF band gap structure" 39 which is an RF open circuit, while being a DC (and/or potentially a low frequency AC) short circuit. This structure can include a thin, typically two-dimensional, pattern of capacitive and inductive elements, which act as miniature parallel resonant circuits which block RF propagation.

In some embodiments, the conductors 20c can be coiled individually or co-wound, or combinations of each. At one end portion, typically a proximal end portion of the segment, the conductors 20c can be selectively connected to the high impedance shield directly or indirectly in a capacitor which act as an RF open and low frequency (DC) open circuit.

FIG. 13B illustrates an exemplary axial sectional view of the device shown in FIG. 13A. FIG. 13C is a cross-sectional view. As shown, a polymer dielectric insulating overcoating 21 can be applied to the lead system 20. As also shown, dielectric/insulation layers 46, 48, 40 may be disposed intermediate the shielding layers 33 (primary shield), 34 (segmented secondary shield), and 36 (segmented tertiary shield). The conductors 20c extend to connector 22 and electrical connections 23 to the IPG or other stimulation, ablation or recording device. Capacitors 24 (FIG. 13A) are not required according to some embodiments of the present invention, as the segmented shielding configurations and inductor lead configuration may provide suitable impedance at high frequency.

FIG. 14 illustrates an electrode arrangement with RF chokes 64rf that can be used with high impedance circuits/segments and configurations described and/or shown herein. Each electrode 100 is typically in communication with at least one of the insulated conductors 20c. At the proximal end of the lead support body 20, the conductors 20c are connected to a connector 22 with electrical connections 23 so as to be connected to the implantable signal generator 102 or to an external circuit, such as an interface circuit 40 during MRI guided lead/cable placement. The lead support body 20 need not be able to provide MRI signals (i.e., it can optionally be configured with an MRI receive antenna). These insulated conductors 20c are typically covered with a polymeric insulator sleeve 61 and a conducting material is cylindrically layered to form the first shielding layer 62 over the insulator. This shielding 62 may be terminated proximal to the electrodes 100 and, in this embodiment, may not be in electrical contact with the conductors and/or the electrodes. A second insulator/polymeric/dielectric layer 63 further insulates this shielding 62 to form multi-core coaxial type cable system, with an impedance that is typically between about 10-100 ohms. The RF chokes 64rf can be integrated or built into the shielding 64 in the form of a second shielding, which is not continuous and has multiple sections each λ/4 or less in length. As shown in FIG. 14, at the proximal end, each section or segment 64s is connected to the primary shielding 62, and the distal end may not be electrically connected to the primary shielding 62, or is connected with a capacitance 164 in between the primary and secondary shielding 62, 64, respectively. A top insulator/polymeric layer 65 can be used to insulate the body 20b, except for the electrodes 25.

As shown by the axial arrow in FIG. 14, the MRI active portion of the antenna 35 may extend between a location where the primary shield 62 terminates and the first electrode $25_1$. However, other antenna 35 configurations may also be used. As shown, the second shield layer 64 comprises a plurality of axially spaced apart RF chokes 64rf. The term "RF chokes" refers to a shielding layer configuration that provides an electrical length of less than or equal to λ/4 (from the perspective of external electromagnetic waves) to inhibit the formation and/or propagation of RF induced current or standing waves in an AC (alternating current, e.g., diathermy applications) or RF exposure environment. The physical length that provides the electrical wavelength may vary depending on the materials used in fabricating the catheter or lead system support body (such as dielectric constant) and the magnetic field in which it is used. In some embodiments, the lead system 20 has a physical length that is greater than 10 cm, typically between about 20 cm to about 150 cm. In some embodiments, the implantable lead segment 50 can also include RF chokes 64rf formed along target regions or along substantially the entire implantable length. In the embodiment shown in FIG. 14, the RF chokes 64rf comprise a plurality of disconnects of the shield 64 and/or discrete electrically isolated second shield segments. In other embodiments, the RF chokes 64rf can include a series of axially spaced apart Balun circuits or other suitable circuit configurations. See, e.g., U.S. Pat. No. 6,284,971, the contents of which are hereby incorporated by reference as if recited in full herein, for additional description of RF inhibiting coaxial cable that can inhibit RF induced current.

As shown in FIG. 14, the second shield layer 64 may be coupled to the first shielding layer 62 at opposing ends of the segments 64s. As shown, one end (typically the proximal end portion) of the disconnected segment 64s is directly coupled to the shielding layer 62 and the other end (typically the distal end portion) is capacitively coupled to the first shielding layer 62. Each segment 64s may be configured to engage the first shield layer 62 in the same manner or in an opposing different electrical manner (not shown).

Figure 15A:
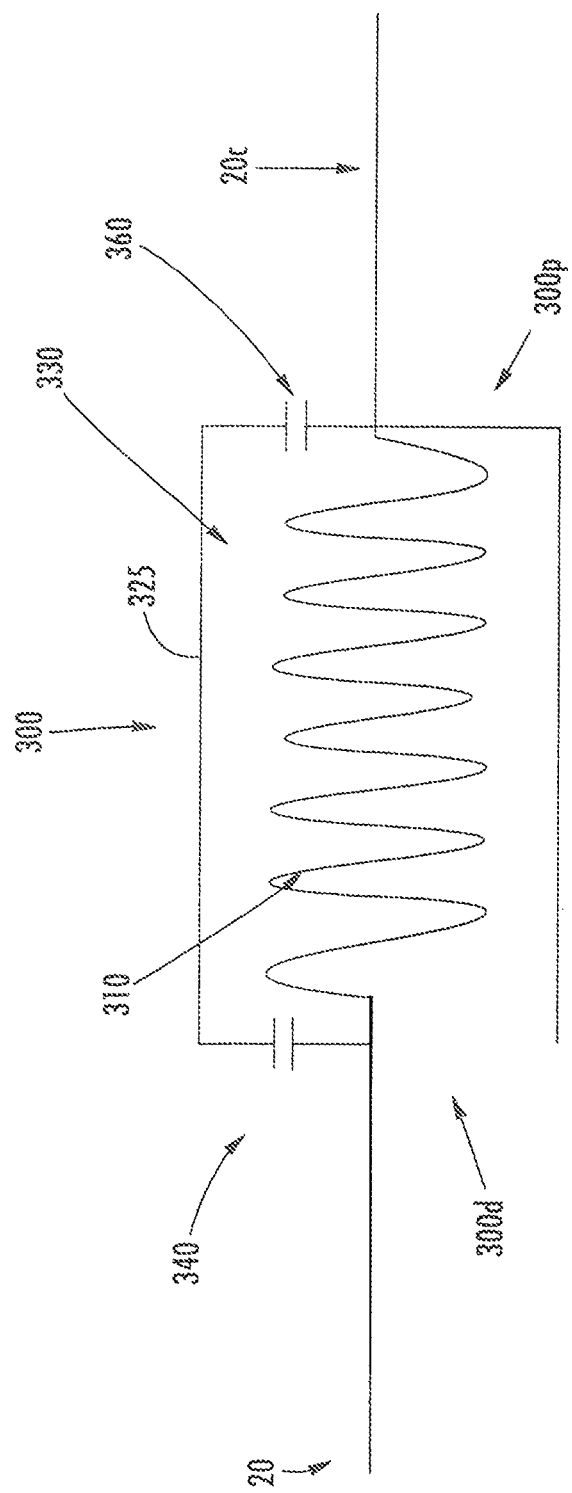
FIG. 15A is a schematic illustration of an RF trap that can be used to form a high impedance segment on a lead according to embodiments of the invention.
Figure 15B:
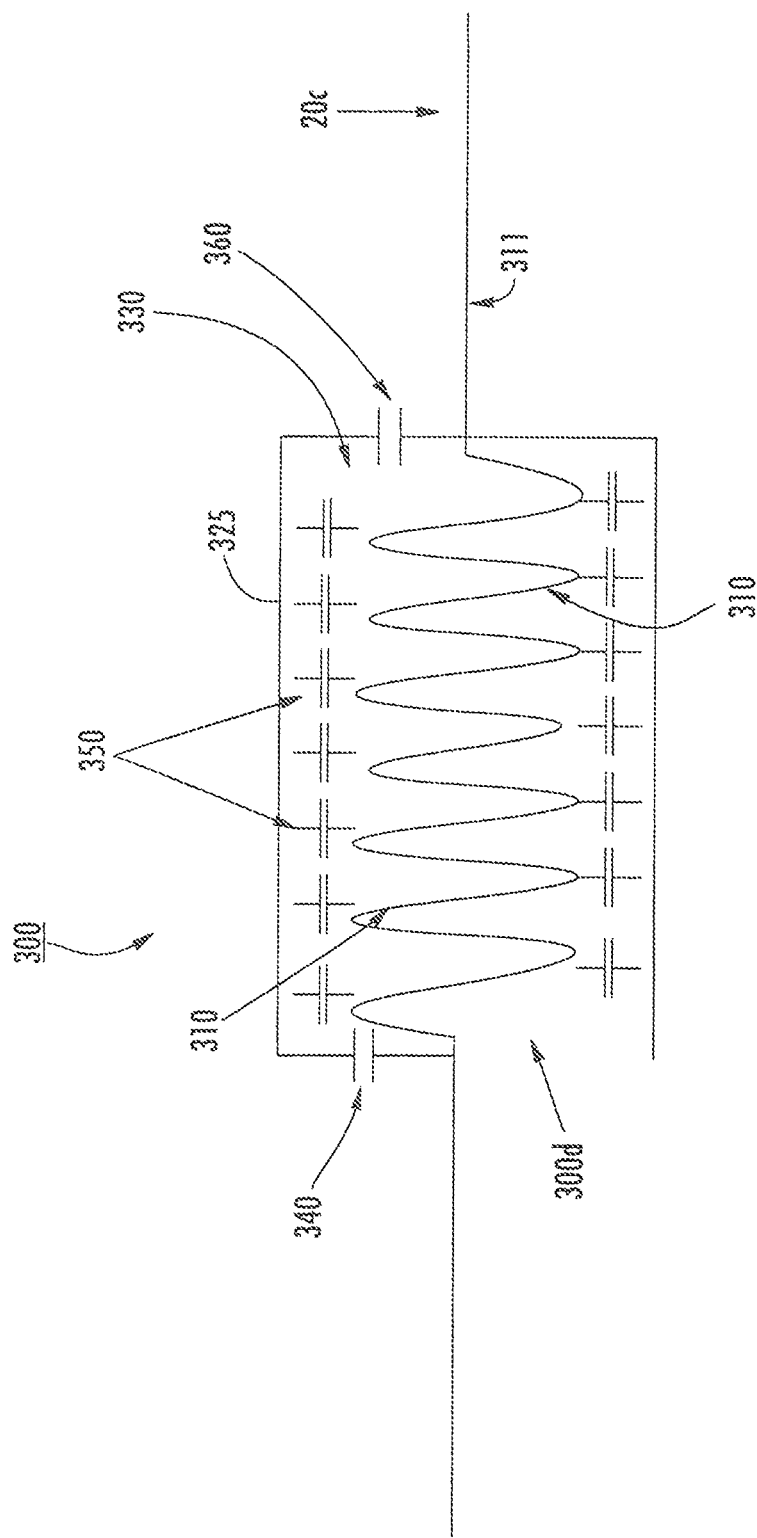
FIG. 15B is a schematic illustration of the RF trap shown in FIG. 15A with the addition of a capacitor connecting the shield and the conductor according to some embodiments of the invention.

FIGS. 15A-15B illustrate lead systems 20 with at least one high impedance segment 300 with associated axially spaced apart proximal and distal portions, 300p, 300d, respectively. The high impedance segment 300 can be described as an RF trap that includes a conductor 20c being coiled to define an inductor 310 within a conductive shield 325 and with an insulator/dielectric material 330 between the inductor 310 and shield 325. The conductor 20c can be in electrical communication with the conductive shield 325 at one end (shown in FIG. 15A as the proximal end portion 300p) of the high impedance segment 300.

The implantable lead system can include multiple high impedance sections or segments 300 along the length of the lead. The high impedance sections or segments are created by arranging the components of the medical device, i.e., the conductor, etc. as an RF trap. These high impedance RF traps inhibit the flow of induced RF current (at the frequency to which the RF trap is tuned) and prevent it from heating tissue adjacent to the electrodes, thus minimizing or preventing RF induced tissue damage. Since the physiological and stimulation signals are at low frequencies (KHz range), the RF trap allows the lower frequency signal(s) to go through, trapping only the higher frequencies of interest to which the traps are tuned.

As shown in FIG. 15A, the conductor 20c can be in electrical communication with the shield at the distal portion of the high impedance segment 300 via a tuning capacitor 340. The high impedance segment 300 (e.g., RF trap) can be tuned to a MRI frequency. The segment 300 can also be configured so that the conductor 20c at the proximal end portion of the segment 300p is connected to the shield 325 via a capacitor 360. Different high impedance segments 300 may be tuned to different MRI frequencies (i.e., 64 MHz and 128 MHz or other standard operating frequencies of commercial MRI scanners). The impedance of the segment 300 can be at least 400 Ohms, typically greater than about 450 Ohms. The at least one high impedance segment 300 can be placed at between about 0.1-12 cm from the electrode(s) 100. The lead 20c can be configured with a straight segment 311 that merges into the coiled segment 310.

In operation, the RF trap 300 with the shield 325, inductor 310 and tuning capacitor 340 form a high impedance parallel resonant circuit at the desired frequency to block RF currents along the conductor. The tuning capacitor can include one or more of a discrete capacitor 340 (FIG. 15A) and/or stray capacitance 350 (FIG. 15B) between the inductor 310 and the shield 325.

FIG. 15B illustrates that the high impedance segment 300 may include stray capacitance 350 that resides between the conductive shield 325 and the inductor 310 through the insulator/dielectric 330. The stray capacitance 350 and/or the discrete capacitor 340 can be used to tune the RF trap to a high-impedance at a desired frequency (range), typically between 1 MHz to 250 MHz. Another capacitor 360 may also be used at the opposing end of the segment 300 to form an RF short (not shown). The high impedance segment 300 can be tuned to achieve high impedance at desired frequencies by varying the length of the trap structure, thereby increasing or decreasing the total capacitance and inductance until the resonant condition is met at the desired frequency. Different segments 300 along a lead length 20 can be tuned to a different (typically MHz) frequency.

Figure 16:
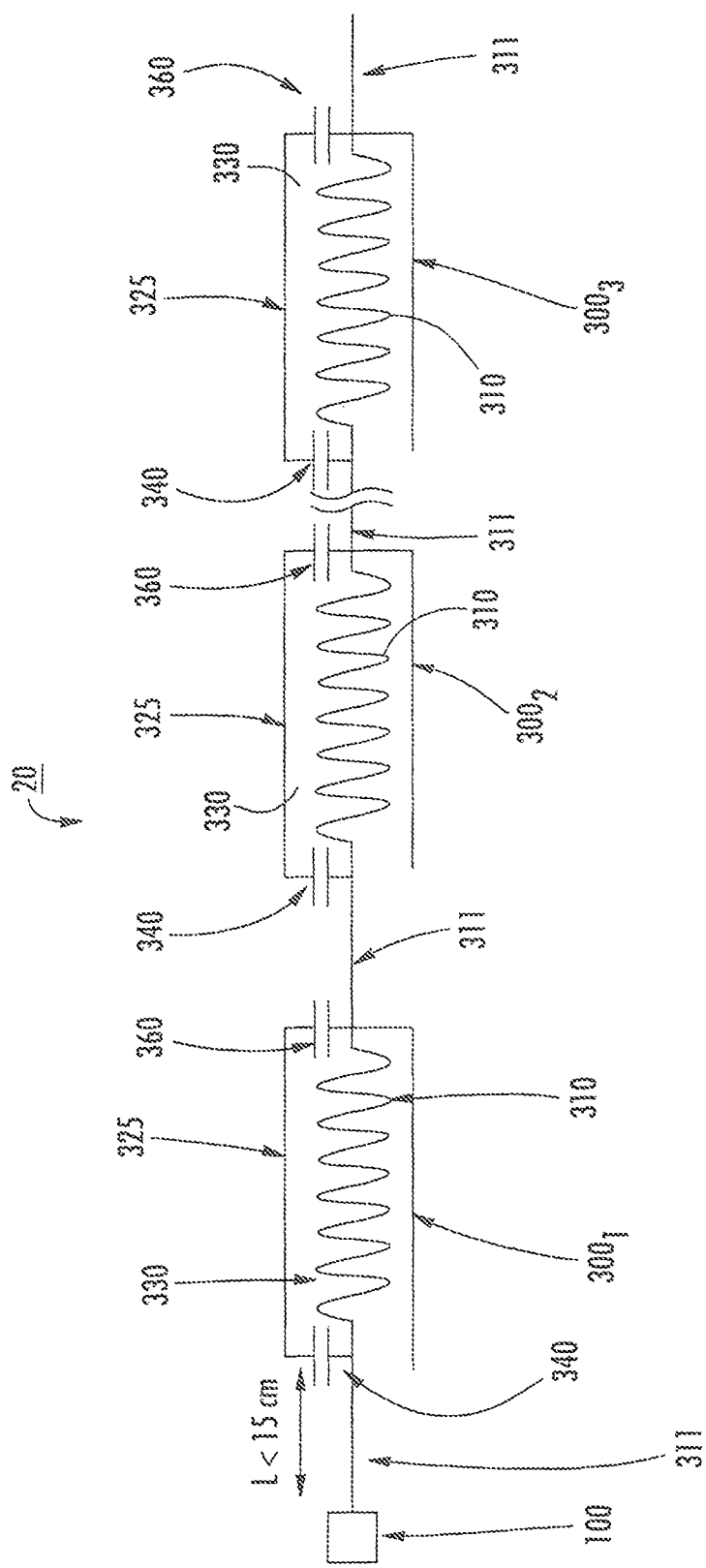
FIG. 16 is a schematic illustration of a long lead with a plurality of axially spaced apart RF traps along a length of a conductor or lead according to embodiments of the invention.

As shown in FIG. 16, a conductive lead 20c can include a plurality of high impedance segments 300 that can be positioned along the length of the lead system 20 at regular or irregular intervals, but typically so that the spacing provides an electrical length of less than about λ/4 therebetween. The RF traps 300 are placed less λ/4 apart, where λ is the wavelength in the medium of the operating frequency, to electrically break the long conductor into multiple sections.

Figure 17:
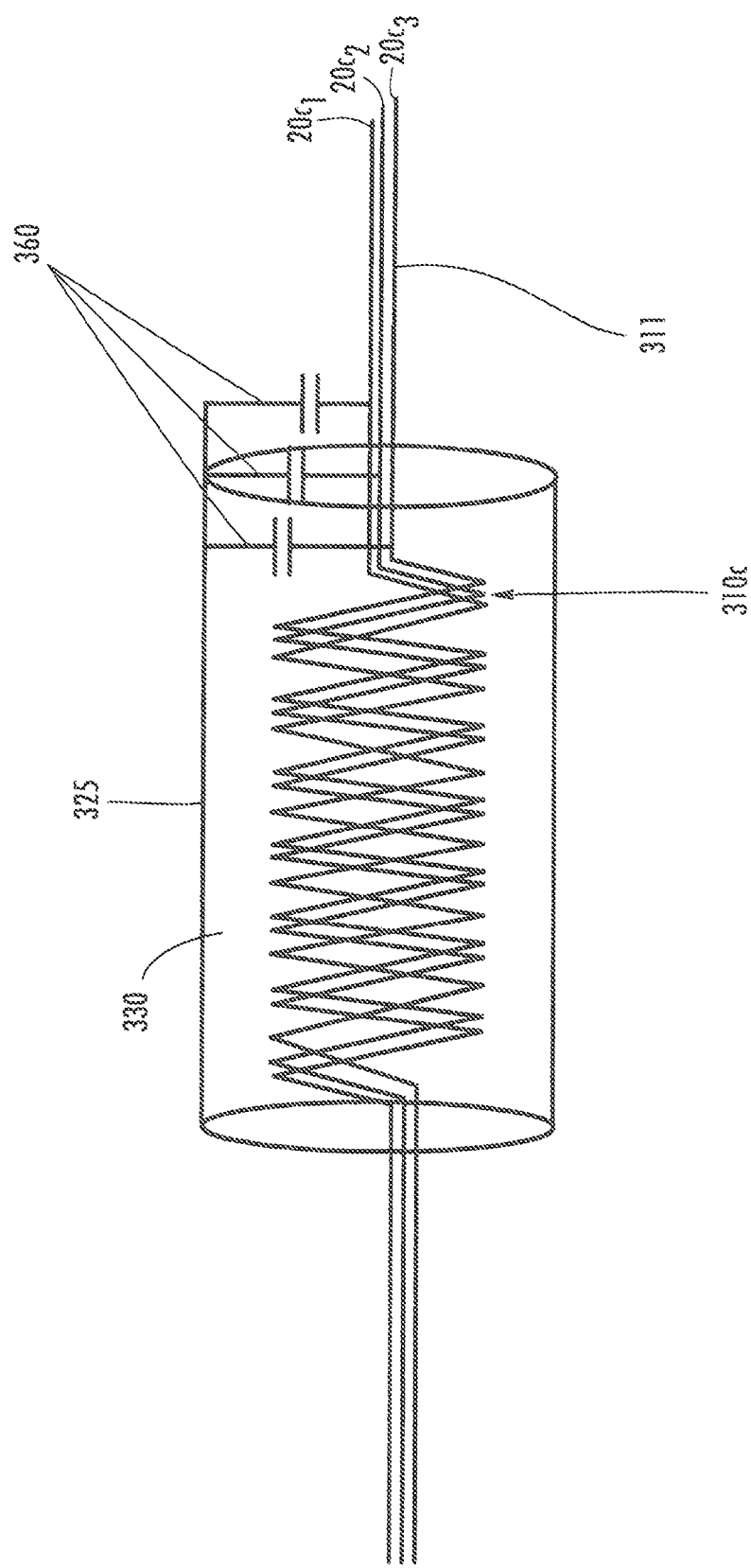
FIG. 17 is a schematic illustration of a lead system with RF traps having co-wound conductors in a common shield according to embodiments of the invention.

FIG. 17 illustrates that a plurality of conductors $20c_1$, $20c_2$, $20c_3$ can be co-wound (see element 310c) and reside within a common flexible shield 325. Each conductor $20c_1$, $20c_2$, $20c_3$ can be electrically connected to the shield 325 at a proximal portion thereof, directly or indirectly, such as using a respective capacitor 360 as shown. The capacitor 360 can provide an RF short. The high impedance segments 300 (RF traps) are placed less than a λ/4 apart from each other at the desired frequency.

When multiple high impedance segments 300 (using, for example RF traps) are incorporated over the length of a device such that the distance between two adjacent traps is less than one-quarter wavelength, this effectively breaks the long conductor into multiple sections, each shorter than a quarter wavelength. The RF current induced on a conductor is a function of length of the conductor at the RF frequency, and when the conductor is shorter than a quarter wavelength, the RF current induced is not large enough and may not cause undue RF deposition RF induced-treating of the tissue.

For a bare copper wire λ/4 in a physiological medium, the length has been measured at about ~8 cm at 64 MHz (1.5 T) and 4 cm at 128 MHz (3 T). For implantable leads where the conductors are insulated with a polymeric layer of about or >0.001 inches thick, and have an electrode exposed to tissue, the temperature change in the tissue adjacent to the electrode due to RF deposition is measured to be less than 1° C. at length less than 15 cm at 1.5 T (64 MHz frequency). When a high impedance segment or section 300 (using one or more RF traps) is incorporated in the length of the conductor 20c, the section 300 can be positioned such that the distal end of the trap 300d is less than 15 cm from one or more of the electrodes 100 and the impedance can be greater than about 450 Ohms at a target MRI frequency, in order to reduce RF deposition induced heating at the electrodes (less than 1° C.).

Thus, in some embodiments, multiple segments 300 with impedance of about or greater than 450 Ohms (at 64 MHz) are placed at distances less than 15 cm apart on a long conductor, which can make the conductor 20c safe to use in MRI at 1.5 T. Similarly if these segments 300 have an impedance of about or greater than 450 Ohms at 128 MHz and are placed <10 cm apart (Length~λ/4 at 128 MHz, or 3 T MRI frequency), it can effectively reduce the extent of heating at the electrode in a 3 T MRI environment.

Different designs of high impedance segments 300 along the length of the leads for multi-conductor lead systems with electrodes are described herein. Such high impedance segments 300 can be placed along the length (less than λ/4 length apart from each other) of the lead 20 to reduce RF deposition at the electrodes 100 and inhibit undue tissue damage.

Figure 18C:
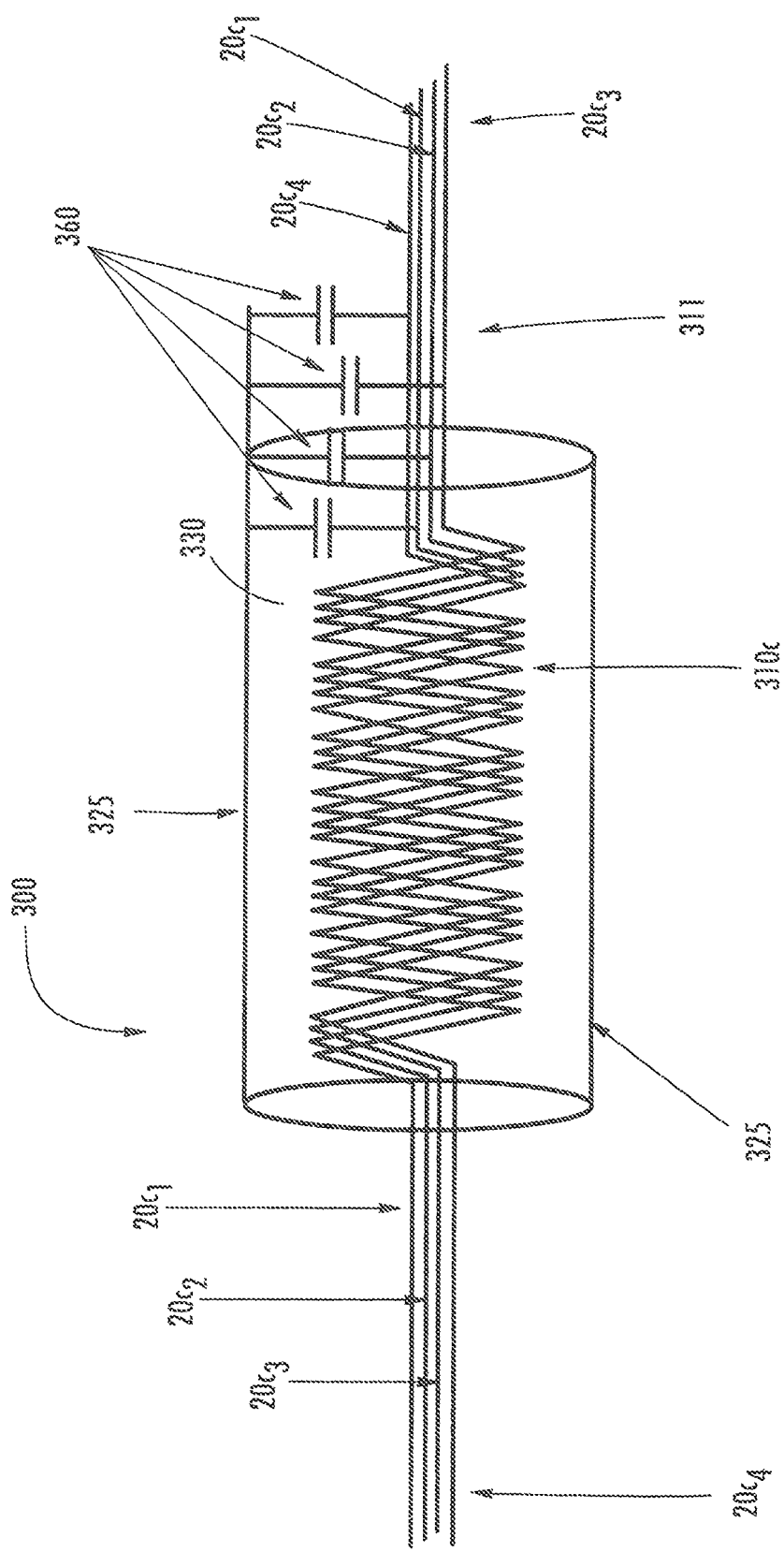
FIG. 18C is a schematic line illustration of the embodiment shown in FIG. 18A.

FIGS. 18A-18C illustrate a high impedance segment 300 with four co-wound conductors/filars $20c_1$-$20c_4$ and a shield 325 placed over the co-wound conductors 310c which is connected to the conductors $20c_1$-$20c_4$ at the proximal end of the trap 300p via respective capacitors 360. The capacitor 360 can have a relatively large capacitance sufficient to act as an RF short and a DC and low frequency (Hz, kHz) open circuit. The connection 370 can be via a metallic trace, small wire or other connection from a linear segment 311 of the conductor 20c to the shield 325 as the conductor 20c merges into a coiled segment 310. A polymeric outer layer 21 can be provided over the shield 325. The lead system 20 can be a flexible lead system and the dielectric material 330 can be provided as a flexible material.

As shown in FIGS. 18A and 18B, for a lead 20 comprising one or more insulated filars/conductors 20c, the filars/conductors 20c can have a straight section 311 followed by a coiled section 310 that forms the inductor. The coiled section 310 may be co-wound with another filar/conductor. A dielectric/insulator 330 can be placed on the coiled section 310 and a shield 325 can be placed on the co-wound conductors separated by the dielectric 330 between them. As shown, at the proximal end portion of the coil 310, the shield 325 is connected (via trace or wire 370) to each conductor $20c_1$-$20c_4$ by a capacitor 360 which acts as an RF short at high frequencies and a DC and low frequency open circuit.

Although the tuning capacitor 340 is shown in various embodiments at a distal portion of the segment 300d and the RF short and low frequency open circuit capacitor 360 is shown at the proximal portion 300p, the reverse orientation may also be used. Also, alternating or different orientations can be used along a length of the lead system 20.

The length of the shielded co-wound segment 300 is such that a high impedance (typically greater than about 450 Ohms) is created at the distal end of the segment 300d between the shield 325 and the conductor(s) 20c at one or more frequencies. Typically, at least one frequency is an MRI frequency, such as about 64 MHz. This high impedance segment 300 created by shielded coiled conductors/inductors, with the shield 325 electrically connected to the conductors 20c at the proximal end portion of the segment 300p, inhibits RF current from flowing along the length of the lead 20. One or more of such segments 300s, tuned to one or more RF frequencies, may be incorporated along the length of the lead. The length of each segment 300 may be between about 0.1-200 cm, typically between about 1-200 cm, and more typically between about 6 cm to about 15 cm.

FIGS. 18A, 18B, 19A and 19B illustrate a high impedance segment 300 with four conductors $20c_1$-$20c_4$. The conductors $20c_1$-$20c_4$ may comprise filars that have a straight section 311 and a coiled section 310. The straight section 311 may be between about 0-15 cm long and a respective coiled section may be between about 1-150 cm long. An insulator/dielectric material 330 with dielectric constant>1 separates the conductors 20c (coiled and straight sections, 310, 311) and the shield 325 is placed over the insulated conductors $20c_1$-$20c_4$. The high impedance section 300 may be between about 1-150 cm long.

Figures 19A, 19B:
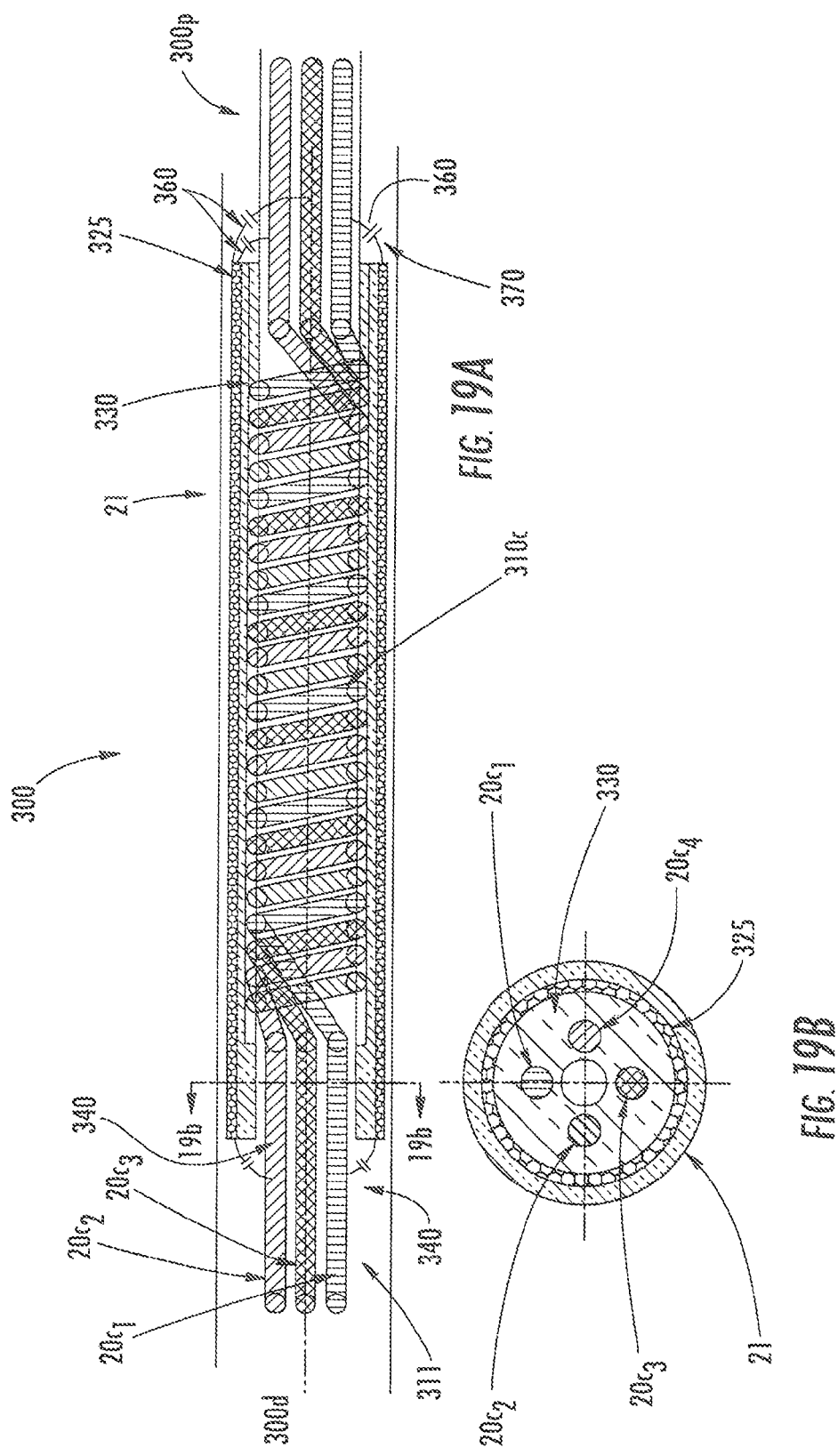
FIG. 19A is a partial cutaway side view of a multi-lead system with an RF trap having co-wound conductors/filars with capacitors connecting the respective leads to the conductive shield at two locations according to some embodiments of the invention.
FIG. 19B is a cross-section view taken along lines 19B-19B in FIG. 19A.

In the embodiments shown in both FIGS. 18A and 19A, at the proximal end of the high impedance section 300p, the shield 325 is connected to the conductors 20c via capacitors 360, typically having a value between about 100 pF to 10000 μF, using a trace or thin wire 370 to facilitate the connection. This capacitor 360 creates an RF short at high frequencies and a low frequency and DC open circuit and inhibits the stimulation current from getting shorted in the shield 325. The diameter of the lead system 20 can be between about 0.10-19 mm, typically between about 0.5-6 mm, and can be varying in different sections of the lead. The lead 20 may be substantially flat, elliptical, circular, rectangular, or square in cross-sectional shape.

Figure 19C:
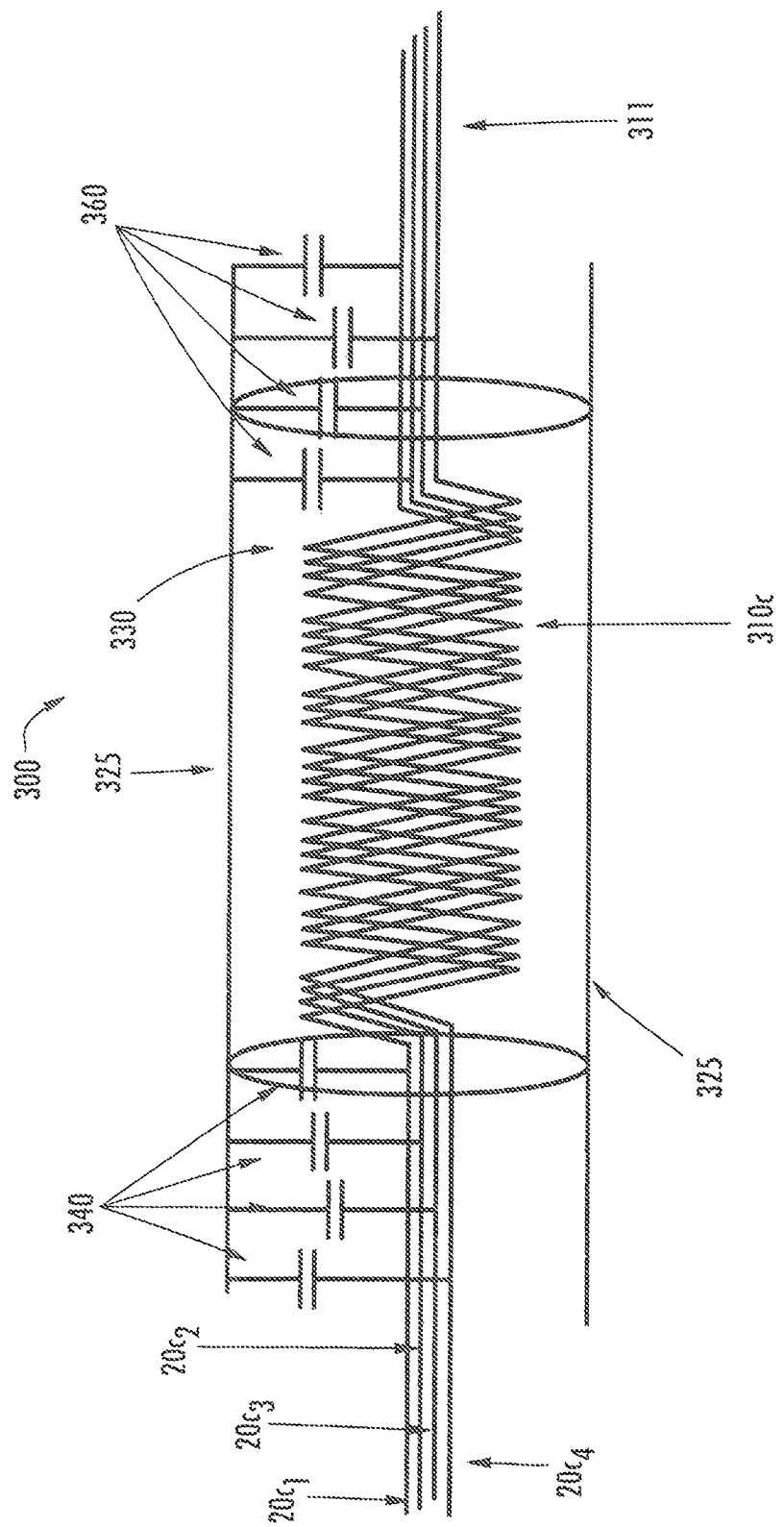
FIG. 19C is a schematic line illustration of the embodiment shown in FIG. 19A.

FIGS. 19A-19C illustrate a lead system 20 with at least one high impedance segment 300 similar to that shown in FIGS. 18A and 18B, but with the conductors 20c connected to the shield 325 via capacitors 340, 360 at both a distal and proximal end portion 300d, 300p of the high impedance segment 300. At one end, for example, the proximal end as shown, the capacitances 360 are large, representing an RF short circuit at high frequency but low frequency open circuit at low frequencies. At the other end, the capacitances 340 are adjusted so that the inductance-shield-capacitance combination forms a high impedance circuit. The inductance and the capacitance are adjusted such that the high impedance segment 300 is tuned to a high impedance at desired frequency or frequencies, where one of these frequencies is an MRI frequency. This design can control the length of the segment 300 (RF trap) to a desired length, such as, for example, less than λ/4 (<10 cm at the desired frequency in physiological medium). A high impedance segment 300 is tuned to a desired frequency by adjusting the values of the parallel resonant circuit created by the RF trap capacitors 360 (and 350 shown in FIG. 15B, where used) and the inductance of the coiled filars 310. This configuration can adjust the length of the segment 300 (RF trap) and the impedance at a RF frequency of interest. One or more segments 300 tuned to one or more MRI frequencies can be placed along the length of the lead 20.

Again, it is noted that in some embodiments, at one end, either the distal or proximal end, the capacitances of the capacitor(s) 360 are sufficiently large to represent an RF short at high frequency but a low frequency open circuit at low frequency. At the opposing other end, the capacitances 340 are adjusted (tuned) so that the inductance-shield-capacitance combination forms the high impedance.

FIGS. 20A and 20B show a high impedance segment 300 with an RF trap with a single one of the four ($20c_1$-$20c_2$) conductors 20c connected to the shield 325 at a proximal portion of the segment 300p. Multiple segments 300 with RF traps similar to the one shown can be placed along the length of the lead 20 and a single different one or pairs or other combinations of the conductors 20c can be serially connected to the shield 325 per different RF trap location, so that each conductor 20c has been connected to the shield 325 at least once before it reaches an electrode 100.

The high impedance segment 300, shown in FIGS. 20A-20C, includes a plurality of co-wound conductors $20c_1$-$20c_2$, wherein only one conductor is connected to the shield 325 at a time. The shield 325 is connected to only one conductor per segment 300 (via a capacitor or directly). In a long lead, the series of segments 300 can be incorporated along the length of the lead 20 and each segment 300 can be designed such that the each conductor 20c is connected to the shield 325 at least once over the length of the lead. In this lead design, the number of segments 300 along the length of the lead 20 can at least equal the number of conductors 20c in the lead.

Figure 21A:
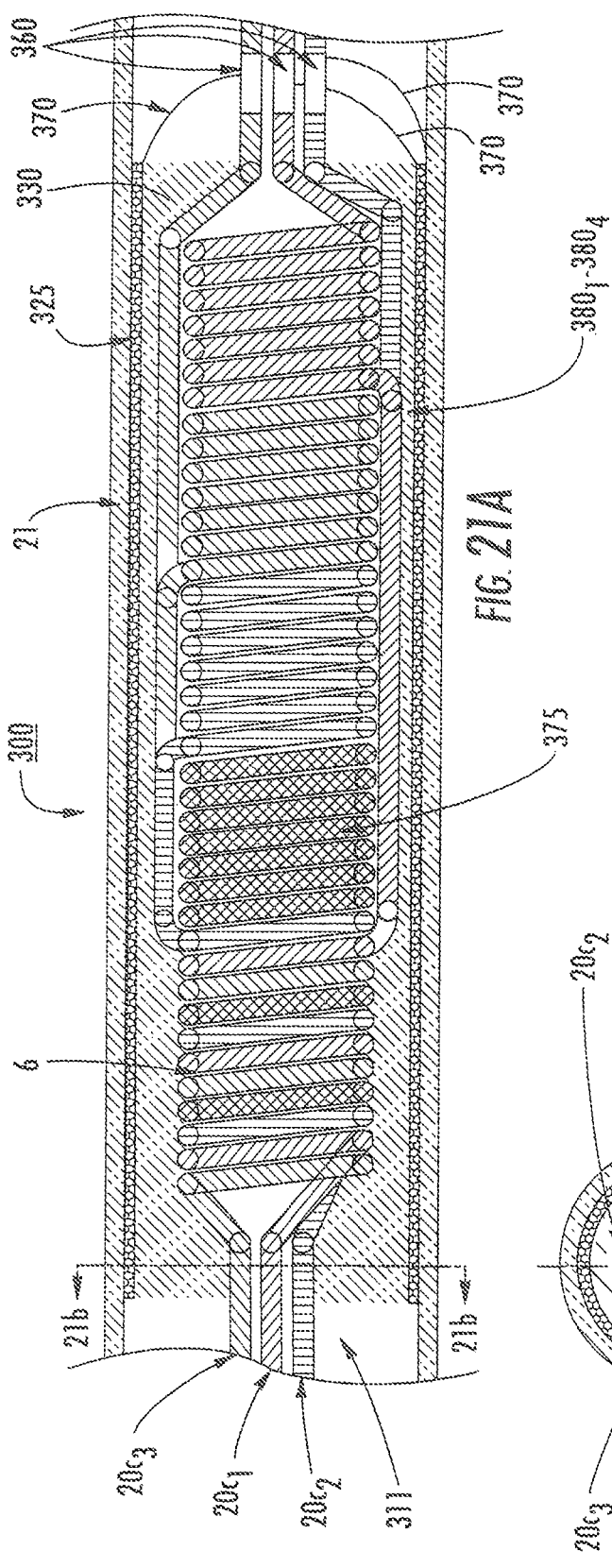
FIG. 21A is a partial cutaway side view of a system with an RF trap having conductors coiled both separately and co-wound according to some embodiments of the invention.
Figure 21B:
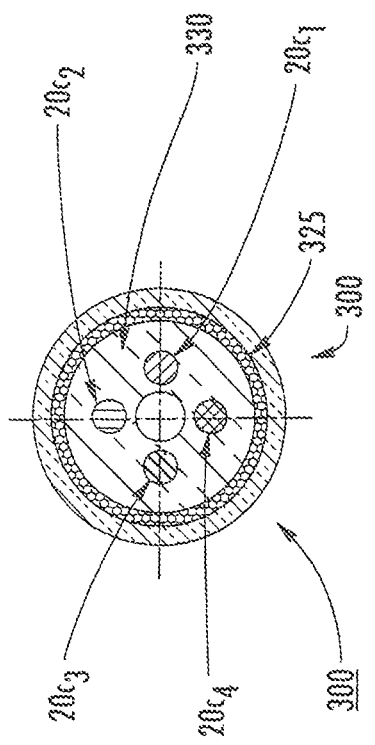
FIG. 21B is a cross-section view taken along lines 21B-21B in FIG. 21A.
Figure 21C:
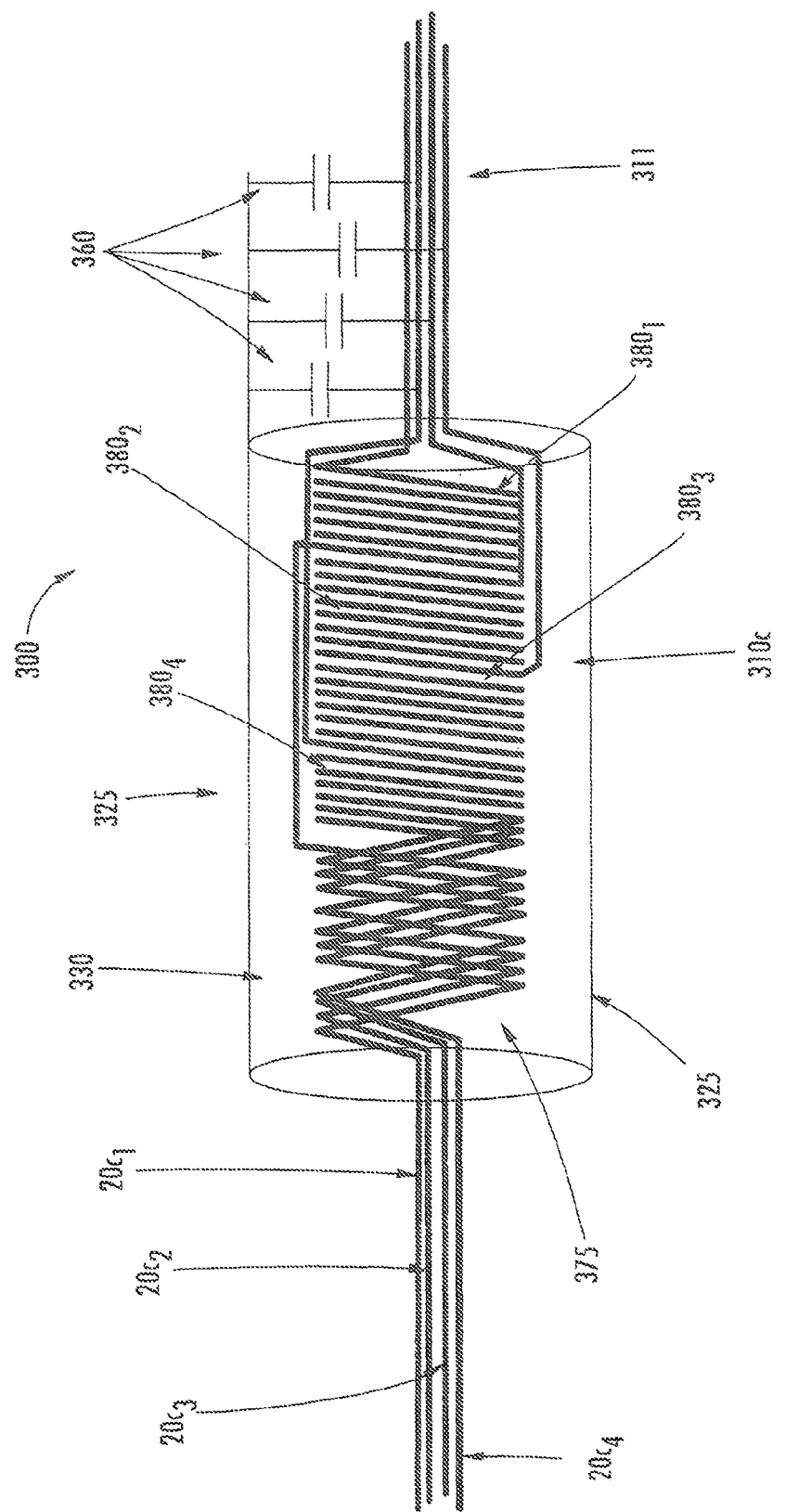
FIG. 21C is a schematic line illustration of the embodiment shown in FIG. 21A.

FIGS. 21A-21C illustrate a high impedance segment 300 with an RF trap having conductors 20c coiled in two different manners: a co-wound segment 375 and a discretely coiled segment 380 (shown as four discrete segments $380_1$, $380_2$, $380_3$, $380_4$, one for each conductor $20c_1$-$20c_4$) under the same shield 325. The segment 375 can be described as having a common co-wound configuration at a common axially extending location. However, one or more of the conductors 20c can be co-wound with one or more other conductors for substantially the entire length of the segment 300 without having an individual or discrete coiled segment 380 in the high impedance segment 300 (i.e., can be co-wound with less than all of the conductors) at a portion of the length of the segment 300

The shield 325 can be connected to at least one of the conductors 20c at the proximal end 300d directly or indirectly. As shown, a connection 370 connects each conductor $20c_1$-$20c_4$ via respective capacitors 360 to the shield 325. Although not shown, one or more of the conductors 20c may be connected to the shield 325 at a distal end of the segment 300 via a capacitor 340.

Figure 22:
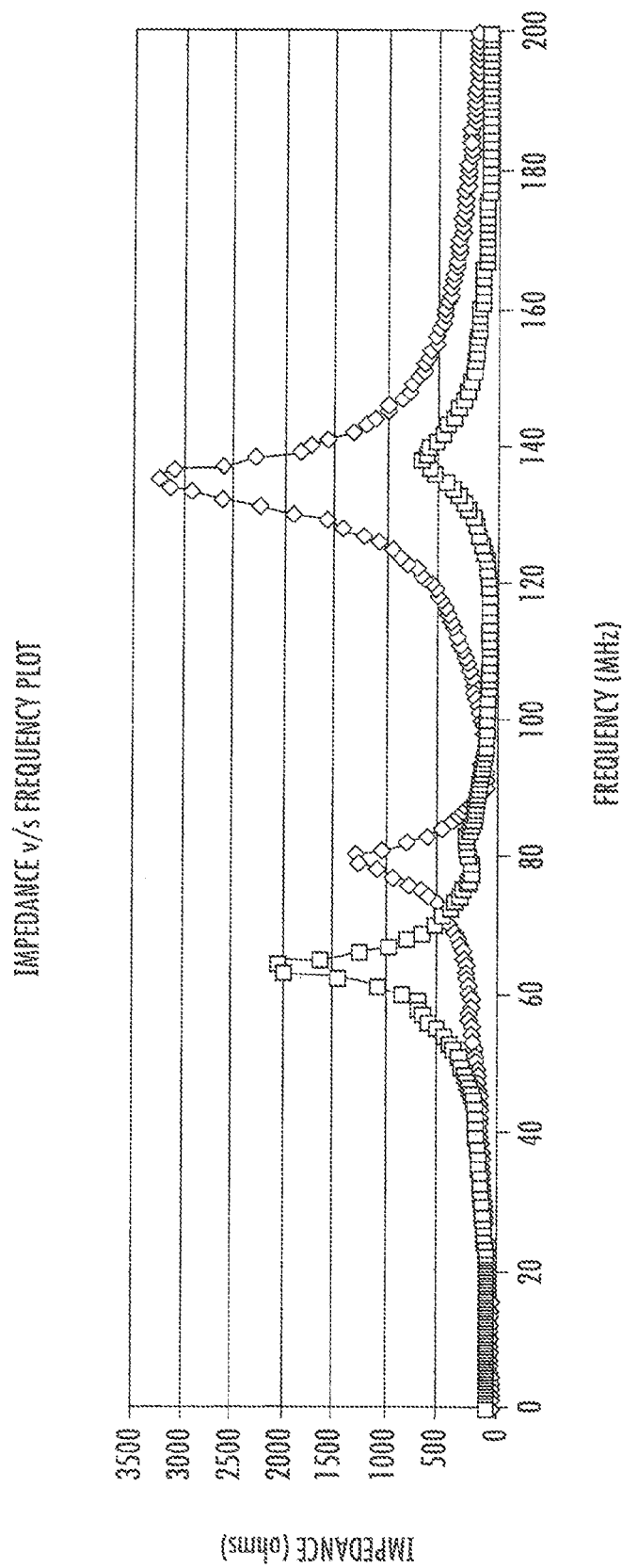
FIG. 22 is a graph of impedance (Ohms) versus frequency (MHz) for the embodiment shown in FIGS. 21A and 21B.

The length of the individual coiled inductors may not be the same on all conductors and is a function of location with respect to other inductors in the segment 300 of the RF trap. This arrangement can be used to create a high impedance at the distal end of the RF trap at one or more frequencies (both in MHz) as shown in FIG. 22. One or both of these frequencies is an MRI frequency.

The length of each individual coiled section 380 and co-wound section 375 can be 0.1-5.0 cm depending on the diameter of the coiled inductor. The spacing between the individually coiled inductors $380_1$-$380_4$ may be between about 0.1-2 cm. This configuration allows a high impedance segment to generate high impedance at a plurality of MHz frequencies, where at least one frequency is an MRI frequency as shown in FIG. 22.

In some embodiments, the conductors or other metallic components of the lead systems 20 may include one or more of: Nitinol, Cobalt-Chromium alloy, MP35N alloy, gold, silver, copper, platinum, platinum-iridium alloy, and other non ferromagnetic materials which will not cause a susceptibility artifact in MRI or magnetically respond to a high field magnet associated with MRI scanners.

Polymeric components can comprise polyurethane, fluorinated ethylene copolymer (FEP, ETFE), PTFE (Teflon), Nylon, PEBAX, polyethylene, polypropylene, and the like. As discussed above, the polymer may be filled with a metallic powder or other fillers.

The conductive shield material may be metallic or conductive non-metallic and may be braided, coiled or deposited over the insulation layer 330 over the inductors 325. The capacitors 340, 360 may comprise semiconductor chip capacitors. Although the exemplary materials are described with respect to embodiments described in FIGS. 15-22, the same materials can be used with respect to other embodiments described herein.

FIG. 22 is a graph of impedance vs. frequency characteristics for the embodiment of the lead system 20 shown in FIGS. 21A and 21B. High impedance is observed at two frequencies. The impedance and frequency are a function of individual inductors and spacing between them. It is contemplated that the design can be configured to generate high impedance at a plurality of frequencies in the MHz range, allowing the lead system or device to be compatible with two or more different field strength MRI scanners (i.e., 1.5 T and at least one other higher field system such as a 2.0 T, 3.0 T or even 9.0 T system).

Embodiments of the invention can be configured to reduce heating at an end of the shield 325 at the distal portion 300d of the high impedance segment (RF trap) 300. The impedance of the RF trap is a function of the inductance of the inductor and the capacitance between the shielded inductor. To achieve impedance>450 Ohms on an inductor of small diameter (typically less than about 1 mm) with more than one conductor 20c co-wound, the length of the segment 300 (RF trap) may sometimes exceed 15 cm. The lead system 20 can be configured with supplemental high impedance segments 300 similar to those described herein with respect to the conductors, or RF chokes, balun circuits and the like may be incorporated on or in the shield 325. Alternatively, or additionally, discrete tubular resistors may be incorporated on or into the shield 325 to inhibit RF deposition at the distal ends of the shield. Alternatively or additionally, a thickness of the outer insulator/polymer layer 21 can be increased to reduce the likelihood of undue RF deposition at the distal end of the shield.

In the drawings and specification, there have been disclosed embodiments of the invention and, although specific terms are employed, they are used in a generic and descriptive sense only and not for purposes of limitation, the scope of the invention being set forth in the following claims. Thus, the foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. In the claims, means-plus-function clauses, where used, are intended to cover the structures described herein as performing the recited function and not only structural equivalents but also equivalent structures. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

What is claimed and desired to be protected by Letters Patent of the United States is:

1. An MRI/RF compatible medical lead, comprising:
   an elongate flexible body;
   a plurality of conductors extending along the elongate flexible body, each of the conductors comprising a plurality of axially spaced apart coiled segments and a plurality of linear segments with the linear segments disposed between adjacent coiled segments;
   at least two electrodes disposed on a distal portion of the elongate flexible body, each electrode coupled to a different one of the plurality of conductors;
   wherein the lead defines a plurality of high impedance RF traps spaced apart along a length of the elongate flexible body, each high impedance RF trap comprising at least one coiled segment of each of two or more of the plurality of conductors, wherein each high impedance RF trap is configured and arranged to inhibit flow of induced RF current at a first frequency, wherein the first frequency is at least 1 MHz, and each high impedance RF trap is configured and arranged to allow stimulation signals having a frequency of 1 kHz or less to pass through the high impedance RF trap.

2. The lead of claim 1, further comprising a plurality of spaced apart capacitors disposed between the plurality of conductors.

3. The lead of claim 2, wherein the at least two electrodes comprise at least three axially spaced apart electrodes and the plurality of conductors comprises a first conductor, a second conductor, and a third conductor, and wherein some of the plurality of capacitors are arranged to extend between the first and second conductors and others of the plurality of capacitors are arranged to extend between the second and third conductors.

4. The lead of claim 3, wherein the capacitors between the first and second conductors are axially offset from the capacitors between the second and third conductors.

5. The lead of claim 2, wherein the spaced apart capacitors are substantially regularly spaced apart axially.

6. The lead of claim 1, the elongate flexible body comprises an electrically insulating biocompatible coating.

7. The lead of claim 1, wherein first frequency is in a range from 1 to 150 MHz.

8. The lead of claim 1, wherein each high impedance RF trap is configured and arrange to allow stimulation signals having a frequency of 50 kHz or less to pass through the high impedance RF trap.

9. The lead of claim 1, further comprising
a dielectric disposed over at least one of the coiled segments; and
a conductive shield disposed over the dielectric.

10. The lead of claim 9, farther comprising a capacitor electrically connecting at least one of the coiled segments to the conductive shield to define an RF short and low frequency open circuit.

11. A medical device, comprising:
an implantable pulse generator; and
the MRI/RF compatible medical lead of claim 1.

12. An MRI/RF compatible medical lead, comprising:
an elongate flexible body;
a first electrode disposed near an end of the flexible body;
a second electrode disposed near the end of the flexible body;
a first axially extending conductor extending along the flexible body and coupled to the first electrode;
a second axially extending conductor extending along the flexible body and coupled to the second electrode; and
a plurality of spaced apart capacitors;
wherein, at each of a plurality of intermediate locations along at least a major portion of a length of the lead, at least one of the capacitors is disposed between the first and second axially extending conductors to define a plurality of high impedance circuit segments, each high impedance circuit segment comprising at least a portion of the first axially extending conductor, at least a portion of the second axially extending conductor, and at least one of the plurality of spaced apart capacitors, wherein each of the plurality of high impedance circuit segments is configured as an RF trap that inhibits flow of induced RF current at a target range of high frequencies to inhibit heating tissue adjacent to the first and second electrodes, wherein high frequencies are frequencies at or above 1 MHz, whereby the lead has a high impedance at the target range of high frequencies and a low impedance at low frequencies.

13. The lead of claim 12, further comprising
a third electrode disposed near the end of the flexible body; and
a third axially extending conductor extending along the flexible body and coupled to third electrode;
wherein a plurality of the capacitors are disposed between the second and third conductors.

14. The lead of claim 13, wherein the capacitors between the first and second conductors are axially offset from the capacitors between the second and third conductors.

15. The lead of claim 12, wherein at least one of the first and second conductors defines an inductor that is in electrical communication with at least two of the capacitors.

16. The lead of claim 12, wherein the spaced apart capacitors are substantially regularly spaced apart axially.

17. The lead of claim 12, wherein at least some of the spaced apart capacitors are axially spaced apart at irregular intervals.

18. The lead of claim 12, wherein the lead is formed entirely from non-magnetic materials.

19. A medical device, comprising:
an implantable pulse generator; and
the MRI/RF compatible medical lead of claim 12.

20. A system, comprising:
an implantable pulse generator comprising a housing; a high impedance decoupling circuit disposed in the housing; and a controller disposed in the housing; and
at least one implantable lead coupleable to the implantable pulse generator and to the decoupling circuit, the lead comprising at least one electrode disposed thereon;
wherein the controller is configured to selectively activate the decoupling circuit to provide, when the lead is coupled to the implantable pulse generator, a high impedance to the lead at high radio frequencies and a low impedance at low radio frequencies, wherein the controller is remotely controllable to activate the decoupling circuit to provide the high impedance.

* * * * *